(12) United States Patent
Dove et al.

(10) Patent No.: US 10,092,399 B2
(45) Date of Patent: *Oct. 9, 2018

(54) METHODS OF CONDITIONING SHEET BIOPROSTHETIC TISSUE

(71) Applicant: Edwards Lifesciences Corporation, Irvine, CA (US)

(72) Inventors: Jeffrey S. Dove, Santa Ana, CA (US); Bin Tian, Irvine, CA (US); Ralph Schneider, Trabuco Canyon, CA (US); Jeffrey S. Cohen, Irvine, CA (US); Ivan Jankovic, Costa Mesa, CA (US); John F. Migliazza, Belmont Shores, CA (US); Gregory A. Wright, Orange, CA (US); James M. Young, Ladera Ranch, CA (US); Louis A. Campbell, Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,990

(22) Filed: Nov. 21, 2016

(65) Prior Publication Data

US 2017/0071731 A1 Mar. 16, 2017

Related U.S. Application Data

(63) Continuation of application No. 13/950,154, filed on Jul. 24, 2013, now Pat. No. 9,498,288, which is a continuation of application No. 13/069,827, filed on Mar. 23, 2011, now Pat. No. 8,846,390.

(60) Provisional application No. 61/381,858, filed on Sep. 10, 2010, provisional application No. 61/316,801, filed on Mar. 23, 2010.

(51) Int. Cl.
| | |
|---|---|
| *A61F 2/24* | (2006.01) |
| *A61L 27/50* | (2006.01) |
| *A61B 18/20* | (2006.01) |
| *A61L 27/36* | (2006.01) |
| *B65B 55/18* | (2006.01) |
| *B65B 63/02* | (2006.01) |
| *A61F 2/02* | (2006.01) |
| *A61F 2/30* | (2006.01) |

(52) U.S. Cl.
CPC ............ *A61F 2/2415* (2013.01); *A61B 18/20* (2013.01); *A61F 2/2409* (2013.01); *A61F 2/2418* (2013.01); *A61L 27/3604* (2013.01); *A61L 27/3625* (2013.01); *A61L 27/3691* (2013.01); *A61L 27/507* (2013.01); *B65B 55/18* (2013.01); *B65B 63/02* (2013.01); *A61F 2/02* (2013.01); *A61F 2/24* (2013.01); *A61F 2002/30324* (2013.01); *A61F 2250/0036* (2013.01); *A61L 2300/60* (2013.01); *A61L 2430/20* (2013.01)

(58) Field of Classification Search
CPC .. A61B 18/20; A61F 2002/30324; A61F 2/02; A61F 2/24; A61F 2/2415; A61L 2300/60; A61L 2430/20; A61L 27/3604; A61L 27/3691; A61L 27/507

USPC ............ 623/2.13; 600/36; 606/14; 264/138, 264/299; 435/325

See application file for complete search history.

(56) References Cited

U.S. PATENT DOCUMENTS

| | | |
|---|---|---|
| 2,393,580 A | 1/1946 | Weiskopf |
| 2,484,813 A | 10/1949 | Bower |
| 2,567,929 A | 9/1951 | Fessenden |
| 3,002,895 A | 10/1961 | Freedman |
| 3,093,439 A | 6/1963 | Bothwell |
| 3,870,789 A | 3/1975 | Mikat |
| 3,927,422 A | 12/1975 | Sawyer |
| 3,961,097 A | 6/1976 | Gravlee, Jr. |
| 3,966,401 A | 6/1976 | Hancock et al. |
| 4,050,893 A | 9/1977 | Hancock et al. |
| 4,067,091 A | 1/1978 | Backman |
| 4,082,507 A | 4/1978 | Sawyer |
| 4,120,649 A | 10/1978 | Schechter |
| 4,120,991 A | 10/1978 | Ornstein et al. |
| 4,197,658 A | 4/1980 | Fraser |
| 4,207,689 A | 6/1980 | Romera-Sierra et al. |
| 4,294,753 A | 10/1981 | Urist |
| 4,320,157 A | 3/1982 | von Hagens |
| 4,323,358 A | 4/1982 | Lentz et al. |
| 4,328,256 A | 5/1982 | Romero-Sierra et al. |
| 4,347,671 A | 9/1982 | Dias et al. |
| 4,350,492 A | 9/1982 | Wright et al. |

(Continued)

FOREIGN PATENT DOCUMENTS

| | | |
|---|---|---|
| CN | 1281402 A | 1/2001 |
| EP | 0169259 A1 | 1/1986 |

(Continued)

OTHER PUBLICATIONS

International Search Report from corresponding PCT Case No. PCT/US2011/029654 dated Dec. 23, 2011.

(Continued)

*Primary Examiner* — Janet L Epps-Smith
(74) *Attorney, Agent, or Firm* — Sheppard Mullin Richter & Hampton

(57) ABSTRACT

Methods for the conditioning of bioprosthetic material employ bovine pericardial membrane. A laser directed at the fibrous surface of the membrane and moved relative thereto reduces the thickness of the membrane to a specific uniform thickness and smoothes the surface. The wavelength, power and pulse rate of the laser are selected which will smooth the fibrous surface as well as ablate the surface to the appropriate thickness. Alternatively, a dermatome is used to remove a layer of material from the fibrous surface of the membrane. Thinning may also employ compression. Stepwise compression with cross-linking to stabilize the membrane is used to avoid damaging the membrane through inelastic compression. Rather, the membrane is bound in the elastic compressed state through addition cross-linking. The foregoing several thinning techniques may be employed together to achieve strong thin membranes.

34 Claims, 5 Drawing Sheets

(56) References Cited

U.S. PATENT DOCUMENTS

| | | |
|---|---|---|
| 4,372,743 A | 2/1983 | Lane |
| 4,378,224 A | 3/1983 | Nimni et al. |
| 4,402,697 A | 9/1983 | Pollock et al. |
| 4,405,327 A | 9/1983 | Pollock |
| 4,477,930 A | 10/1984 | Totten et al. |
| 4,481,009 A | 11/1984 | Nashef |
| 4,553,974 A | 11/1985 | Dewanjee |
| 4,599,084 A | 7/1986 | Nashef |
| 4,624,822 A | 11/1986 | Arru et al. |
| 4,647,283 A | 3/1987 | Carpentier et al. |
| 4,648,881 A | 3/1987 | Carpentier et al. |
| 4,655,773 A | 4/1987 | Grassi |
| 4,676,070 A | 6/1987 | Linner |
| 4,729,139 A | 3/1988 | Nashef |
| 4,729,766 A | 3/1988 | Bergentz et al. |
| 4,753,652 A | 6/1988 | Langer et al. |
| 4,758,151 A | 7/1988 | Arru et al. |
| 4,759,758 A | 7/1988 | Gabbay |
| 4,770,665 A | 9/1988 | Nashef |
| 4,776,853 A | 10/1988 | Klement et al. |
| 4,786,287 A | 11/1988 | Nashef et al. |
| 4,793,344 A | 12/1988 | Cumming et al. |
| 4,800,603 A | 1/1989 | Jaffe |
| 4,813,964 A | 3/1989 | Dixon et al. |
| 4,831,065 A | 5/1989 | Pietsch et al. |
| 4,838,888 A | 6/1989 | Nashef |
| 4,865,871 A | 9/1989 | Livesey et al. |
| 4,885,005 A | 12/1989 | Nashef et al. |
| 4,891,319 A | 1/1990 | Roser |
| 4,911,713 A | 3/1990 | Sauvage et al. |
| 4,958,008 A | 9/1990 | Petite et al. |
| 4,969,912 A | 11/1990 | Kelman et al. |
| 4,975,526 A | 12/1990 | Kuberasampath et al. |
| 4,976,733 A | 12/1990 | Girardot |
| 4,990,131 A | 2/1991 | Dardik et al. |
| 4,994,030 A | 2/1991 | Glowczewskie, Jr. et al. |
| 4,994,237 A | 2/1991 | Login et al. |
| 4,996,054 A | 2/1991 | Pietsch et al. |
| 5,002,566 A | 3/1991 | Carpentier et al. |
| 5,011,494 A | 4/1991 | von Recum et al. |
| 5,011,913 A | 4/1991 | Benedict et al. |
| 5,024,830 A | 6/1991 | Linner |
| 5,044,165 A | 9/1991 | Linner et al. |
| 5,051,401 A | 9/1991 | Sikes |
| 5,068,086 A | 11/1991 | Sklenak et al. |
| 5,068,100 A | 11/1991 | McClanahan |
| 5,080,670 A | 1/1992 | Imamura et al. |
| 5,094,661 A | 3/1992 | Levy et al. |
| 5,104,405 A | 4/1992 | Nimni |
| 5,108,923 A | 4/1992 | Benedict et al. |
| 5,116,564 A | 5/1992 | Jansen et al. |
| 5,131,908 A | 7/1992 | Dardik et al. |
| 5,147,391 A | 9/1992 | Lane |
| 5,147,514 A | 9/1992 | Mechanic |
| 5,149,621 A | 9/1992 | McNally et al. |
| 5,149,653 A | 9/1992 | Roser |
| 5,154,007 A | 10/1992 | Piunno et al. |
| 5,163,955 A | 11/1992 | Love et al. |
| 5,200,399 A | 4/1993 | Wettlaufer et al. |
| 5,215,541 A | 6/1993 | Nashef et al. |
| 5,275,954 A | 1/1994 | Wolfinbarger et al. |
| 5,279,612 A | 1/1994 | Eberhardt |
| 5,288,288 A | 2/1994 | Lewis et al. |
| 5,290,558 A | 3/1994 | O'Leary et al. |
| 5,296,583 A | 3/1994 | Levy |
| 5,329,846 A | 7/1994 | Bonutti |
| 5,332,475 A | 7/1994 | Mechanic |
| 5,336,616 A | 8/1994 | Livesey et al. |
| 5,368,608 A | 11/1994 | Levy et al. |
| 5,397,353 A | 3/1995 | Oliver et al. |
| 5,423,887 A | 6/1995 | Love et al. |
| 5,424,047 A | 6/1995 | Zwingenberger et al. |
| 5,436,291 A | 7/1995 | Levy et al. |
| 5,437,287 A | 8/1995 | Phillips et al. |
| 5,447,536 A | 9/1995 | Girardot et al. |
| 5,447,724 A | 9/1995 | Helmus et al. |
| 5,460,962 A | 10/1995 | Kemp |
| 5,476,516 A | 12/1995 | Seifter et al. |
| 5,507,813 A | 4/1996 | Dowd et al. |
| 5,509,932 A | 4/1996 | Keogh et al. |
| 5,549,666 A | 8/1996 | Hata et al. |
| 5,554,184 A | 9/1996 | Machiraju |
| 5,556,379 A | 9/1996 | Wolfinbarger |
| 5,558,875 A | 9/1996 | Wang |
| 5,595,571 A | 1/1997 | Jaffe et al. |
| 5,613,982 A | 3/1997 | Goldstein |
| 5,632,778 A | 5/1997 | Goldstein |
| 5,645,587 A | 7/1997 | Chanda et al. |
| 5,674,298 A | 10/1997 | Levy et al. |
| 5,679,112 A | 10/1997 | Levy et al. |
| 5,695,820 A | 12/1997 | Davis et al. |
| 5,697,972 A | 12/1997 | Kim et al. |
| 5,713,953 A | 2/1998 | Vallana et al. |
| 5,716,399 A | 2/1998 | Love |
| 5,720,777 A | 2/1998 | Jaffe et al. |
| 5,720,894 A | 2/1998 | Neev et al. |
| 5,733,339 A | 3/1998 | Girardot et al. |
| 5,746,775 A | 5/1998 | Levy et al. |
| 5,762,600 A | 6/1998 | Bruchman et al. |
| 5,766,520 A | 6/1998 | Bronshtein |
| 5,769,780 A | 6/1998 | Hata et al. |
| 5,770,193 A | 6/1998 | Vacanti et al. |
| 5,773,285 A | 6/1998 | Park |
| 5,776,182 A | 7/1998 | Bruchman et al. |
| 5,782,914 A | 7/1998 | Schankereli |
| 5,782,915 A | 7/1998 | Stone |
| 5,782,931 A | 7/1998 | Yang et al. |
| 5,792,603 A | 8/1998 | Dunkelman et al. |
| 5,843,180 A | 12/1998 | Jaffe et al. |
| 5,843,181 A | 12/1998 | Jaffe et al. |
| 5,843,182 A | 12/1998 | Goldstein |
| 5,855,620 A | 1/1999 | Bishopric et al. |
| 5,856,102 A | 1/1999 | Bierke-Nelson et al. |
| 5,856,172 A | 1/1999 | Greenwood et al. |
| 5,862,806 A | 1/1999 | Cheung |
| 5,865,849 A | 2/1999 | Stone |
| 5,873,812 A | 2/1999 | Ciana et al. |
| 5,879,383 A | 3/1999 | Bruchman et al. |
| 5,882,850 A | 3/1999 | Khor et al. |
| 5,882,918 A | 3/1999 | Goffe |
| 5,899,936 A | 5/1999 | Goldstein |
| 5,902,338 A | 5/1999 | Stone |
| 5,904,718 A | 5/1999 | Jefferies |
| 5,911,951 A | 6/1999 | Girardot et al. |
| 5,913,900 A | 6/1999 | Stone |
| 5,919,472 A | 7/1999 | Trescony et al. |
| 5,921,980 A | 7/1999 | Kim |
| 5,922,027 A | 7/1999 | Stone |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,039,726 A | 3/2000 | Lewis et al. |
| 6,063,120 A | 5/2000 | Stone |
| 6,066,160 A | 5/2000 | Colvin et al. |
| 6,086,580 A | 7/2000 | Mordon et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,126,686 A | 10/2000 | Badylak et al. |
| 6,129,758 A | 10/2000 | Love |
| 6,132,472 A | 10/2000 | Bonutti |
| 6,132,473 A | 10/2000 | Williams et al. |
| 6,132,986 A | 10/2000 | Pathak et al. |
| 6,156,030 A | 12/2000 | Neev |
| 6,156,531 A | 12/2000 | Pathak et al. |
| 6,165,215 A | 12/2000 | Rottenberg et al. |

(56) References Cited

U.S. PATENT DOCUMENTS

| | | | |
|---|---|---|---|
| 6,166,184 | A | 12/2000 | Hendriks et al. |
| 6,174,331 | B1 | 1/2001 | Moe et al. |
| 6,177,514 | B1 | 1/2001 | Pathak et al. |
| 6,190,407 | B1 | 2/2001 | Ogle et al. |
| 6,193,749 | B1 | 2/2001 | Schroeder et al. |
| 6,203,755 | B1 | 3/2001 | Odland |
| 6,206,873 | B1 | 3/2001 | Paolini et al. |
| 6,206,917 | B1 | 3/2001 | Williams et al. |
| 6,210,957 | B1 | 4/2001 | Carpentier et al. |
| 6,214,054 | B1 | 4/2001 | Cunanan et al. |
| 6,214,055 | B1 | 4/2001 | Simionescu et al. |
| 6,231,608 | B1 | 5/2001 | Stone |
| 6,231,614 | B1 | 5/2001 | Yang |
| 6,251,579 | B1 | 6/2001 | Moore et al. |
| 6,254,635 | B1 * | 7/2001 | Schroeder .......... A61L 27/042 623/2.13 |
| 6,258,320 | B1 | 7/2001 | Persing et al. |
| 6,267,786 | B1 | 7/2001 | Stone |
| 6,277,555 | B1 | 8/2001 | Duran et al. |
| 6,287,338 | B1 | 9/2001 | Sarnowski et al. |
| 6,290,991 | B1 | 9/2001 | Roser et al. |
| 6,302,909 | B1 | 10/2001 | Ogle et al. |
| 6,312,474 | B1 | 11/2001 | Francis et al. |
| 6,322,593 | B1 | 11/2001 | Pathak et al. |
| 6,322,994 | B1 | 11/2001 | Reid |
| 6,328,762 | B1 | 12/2001 | Anderson et al. |
| 6,334,873 | B1 | 1/2002 | Lane et al. |
| 6,352,708 | B1 | 3/2002 | Duran et al. |
| 6,364,905 | B1 | 4/2002 | Simpson et al. |
| 6,372,228 | B1 | 4/2002 | Gregory |
| 6,375,680 | B1 | 4/2002 | Carlyle |
| 6,376,244 | B1 | 4/2002 | Atala |
| 6,378,221 | B1 | 4/2002 | Ekholm, Jr. et al. |
| 6,383,732 | B1 | 5/2002 | Stone |
| 6,391,538 | B1 | 5/2002 | Vyavahare et al. |
| 6,394,096 | B1 | 5/2002 | Constantz |
| 6,448,076 | B2 | 9/2002 | Dennis et al. |
| 6,455,309 | B2 | 9/2002 | Stone |
| 6,468,660 | B2 | 10/2002 | Ogle et al. |
| 6,471,723 | B1 | 10/2002 | Ashworth et al. |
| 6,479,079 | B1 | 11/2002 | Pathak et al. |
| 6,482,199 | B1 | 11/2002 | Neev |
| 6,497,725 | B2 | 12/2002 | Williams et al. |
| 6,506,339 | B1 | 1/2003 | Girardot et al. |
| 6,509,145 | B1 | 1/2003 | Torrianni |
| 6,527,979 | B2 | 3/2003 | Constantz |
| 6,528,006 | B1 | 3/2003 | Jansen |
| 6,531,310 | B1 | 3/2003 | Mirsch, II et al. |
| 6,534,004 | B2 | 3/2003 | Chen et al. |
| 6,547,827 | B2 | 4/2003 | Carpentier et al. |
| 6,561,970 | B1 | 5/2003 | Carpentier et al. |
| 6,569,200 | B2 | 5/2003 | Wolfinbarger, Jr. et al. |
| 6,582,464 | B2 | 6/2003 | Gabbay |
| 6,586,006 | B2 | 7/2003 | Roser et al. |
| 6,586,573 | B2 | 7/2003 | Besman et al. |
| 6,589,591 | B1 | 7/2003 | Mansouri et al. |
| 6,605,079 | B2 | 8/2003 | Shanks et al. |
| 6,605,667 | B1 | 8/2003 | Badejo et al. |
| 6,613,278 | B1 | 9/2003 | Mills et al. |
| 6,617,142 | B2 | 9/2003 | Keogh et al. |
| 6,630,001 | B2 | 10/2003 | Duran et al. |
| 6,638,309 | B2 | 10/2003 | Bonutti |
| 6,652,594 | B2 | 11/2003 | Francis et al. |
| 6,653,062 | B1 | 11/2003 | DePablo et al. |
| 6,660,265 | B1 | 12/2003 | Chen et al. |
| 6,676,654 | B1 | 1/2004 | Balle-Petersen et al. |
| 6,676,655 | B2 | 1/2004 | McDaniel |
| 6,682,559 | B2 | 1/2004 | Myers et al. |
| 6,685,940 | B2 | 2/2004 | Andya et al. |
| 6,696,074 | B2 | 2/2004 | Dai et al. |
| 6,734,018 | B2 | 5/2004 | Wolfinbarger, Jr. et al. |
| 6,753,181 | B2 | 6/2004 | Atala |
| 6,764,509 | B2 | 7/2004 | Chinn et al. |
| 6,790,229 | B1 | 9/2004 | Berreklouw |
| 6,797,000 | B2 | 9/2004 | Simpson et al. |
| 6,828,310 | B2 | 12/2004 | Barresi et al. |
| 6,872,226 | B2 | 3/2005 | Cali et al. |
| 6,878,168 | B2 | 4/2005 | Carpentier et al. |
| 6,893,666 | B2 | 5/2005 | Spievack |
| 6,908,591 | B2 | 6/2005 | MacPhee et al. |
| 6,911,043 | B2 | 6/2005 | Myers et al. |
| 6,919,172 | B2 | 7/2005 | DePablo et al. |
| 6,933,326 | B1 | 8/2005 | Griffey et al. |
| 6,939,378 | B2 | 9/2005 | Fishman et al. |
| 7,008,763 | B2 | 3/2006 | Cheung |
| 7,022,119 | B2 | 4/2006 | Hohla |
| 7,037,333 | B2 | 5/2006 | Myers et al. |
| 7,053,051 | B2 | 5/2006 | Hendriks et al. |
| 7,063,726 | B2 | 6/2006 | Crouch et al. |
| 7,078,163 | B2 | 7/2006 | Torrianni |
| 7,087,723 | B2 | 8/2006 | Besman et al. |
| 7,122,356 | B2 | 10/2006 | Keogh et al. |
| 7,141,064 | B2 * | 11/2006 | Scott ................... A61F 2/2412 600/36 |
| 7,143,769 | B2 | 12/2006 | Stoltz et al. |
| 7,147,846 | B2 | 12/2006 | Anderson et al. |
| 7,189,258 | B2 | 3/2007 | Johnson et al. |
| 7,189,259 | B2 | 3/2007 | Simionescu et al. |
| 7,201,771 | B2 | 4/2007 | Lane |
| 7,217,265 | B2 | 5/2007 | Hennings et al. |
| 7,238,200 | B2 | 7/2007 | Lee et al. |
| 7,318,998 | B2 | 1/2008 | Goldstein et al. |
| 7,338,757 | B2 | 3/2008 | Wolfinbarger, Jr. et al. |
| 7,354,749 | B2 | 4/2008 | Fisher et al. |
| 7,358,284 | B2 | 4/2008 | Griffey et al. |
| 7,367,969 | B2 | 5/2008 | Stoltz et al. |
| 7,498,565 | B2 | 3/2009 | Silberberg et al. |
| 7,578,843 | B2 | 8/2009 | Shu |
| 7,579,381 | B2 | 8/2009 | Dove |
| 7,594,974 | B2 | 9/2009 | Cali et al. |
| 7,621,637 | B2 | 11/2009 | Rathjen et al. |
| 7,648,676 | B2 | 1/2010 | Mills et al. |
| 7,682,304 | B2 | 3/2010 | Heyninck-Jantz et al. |
| 7,871,434 | B2 | 1/2011 | Case et al. |
| 7,914,569 | B2 | 3/2011 | Nguyen et al. |
| 7,918,899 | B2 | 4/2011 | Girardot et al. |
| 7,919,112 | B2 | 4/2011 | Pathak et al. |
| 7,955,788 | B2 | 6/2011 | Zilla et al. |
| 7,963,958 | B2 | 6/2011 | Stoltz et al. |
| 7,993,394 | B2 | 8/2011 | Hariton et al. |
| 8,043,450 | B2 | 10/2011 | Cali et al. |
| 8,067,149 | B2 | 11/2011 | Livesey et al. |
| 8,075,615 | B2 | 12/2011 | Eberhardt et al. |
| 8,136,218 | B2 | 3/2012 | Millwee et al. |
| 8,470,022 | B2 | 6/2013 | Johnson |
| 8,672,999 | B2 | 3/2014 | Cali et al. |
| 8,685,185 | B2 | 4/2014 | Guo et al. |
| 8,846,390 | B2 | 9/2014 | Dove et al. |
| 9,498,288 | B2 * | 11/2016 | Dove .................... A61F 2/2415 |
| 2001/0000804 | A1 | 5/2001 | Goldstein et al. |
| 2001/0020191 | A1 | 9/2001 | Williams et al. |
| 2001/0025196 | A1 | 9/2001 | Chinn et al. |
| 2001/0027344 | A1 | 10/2001 | Bonutti |
| 2001/0032024 | A1 | 10/2001 | Cunanan et al. |
| 2001/0039459 | A1 | 11/2001 | Stone |
| 2002/0001834 | A1 | 1/2002 | Keogh et al. |
| 2002/0091441 | A1 | 7/2002 | Guzik |
| 2002/0111532 | A1 | 8/2002 | Pathak et al. |
| 2003/0035843 | A1 | 2/2003 | Livesey et al. |
| 2003/0125805 | A1 | 7/2003 | Johnson et al. |
| 2003/0135284 | A1 | 7/2003 | Crouch et al. |
| 2003/0167089 | A1 | 9/2003 | Lane |
| 2003/0212454 | A1 | 11/2003 | Scott et al. |
| 2003/0229394 | A1 | 12/2003 | Ogle et al. |
| 2004/0024452 | A1 | 2/2004 | Kruse et al. |
| 2004/0030381 | A1 | 2/2004 | Shu |
| 2004/0086543 | A1 | 5/2004 | Keogh et al. |
| 2004/0158320 | A1 | 8/2004 | Simionescu et al. |
| 2004/0193259 | A1 | 9/2004 | Gabbay |
| 2005/0079200 | A1 | 4/2005 | Rathenow et al. |
| 2005/0107773 | A1 | 5/2005 | Bergt et al. |
| 2005/0119736 | A1 | 6/2005 | Zilla et al. |
| 2005/0136510 | A1 | 6/2005 | Hendriks et al. |
| 2005/0137682 | A1 | 6/2005 | Justino |

(56) References Cited

U.S. PATENT DOCUMENTS

| | | |
|---|---|---|
| 2005/0211680 A1 | 9/2005 | Li et al. |
| 2006/0084957 A1 | 4/2006 | Delfyett et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0177426 A1 | 8/2006 | Gibson et al. |
| 2006/0210960 A1 | 9/2006 | Livesey et al. |
| 2006/0217804 A1 | 9/2006 | Dove |
| 2006/0217805 A1 | 9/2006 | Dove |
| 2006/0228391 A1 | 10/2006 | Seyedin et al. |
| 2007/0010804 A1 | 1/2007 | Rathjen et al. |
| 2007/0048340 A1 | 3/2007 | Ferren et al. |
| 2007/0050014 A1 | 3/2007 | Johnson |
| 2007/0073392 A1 | 3/2007 | Heyninck-Jantz et al. |
| 2007/0203576 A1 | 8/2007 | Lee et al. |
| 2007/0254005 A1 | 11/2007 | Pathak et al. |
| 2007/0292459 A1 | 12/2007 | Cooper et al. |
| 2008/0097601 A1* | 4/2008 | Codori-Hurff ............ A61F 2/12 623/8 |
| 2008/0102439 A1* | 5/2008 | Tian ................... A61L 27/3604 435/1.1 |
| 2008/0195123 A1 | 8/2008 | Gainor et al. |
| 2008/0302372 A1 | 12/2008 | Davidson et al. |
| 2009/0041729 A1 | 2/2009 | Wolfinbarger, Jr. et al. |
| 2009/0105813 A1 | 4/2009 | Chambers et al. |
| 2009/0112309 A1 | 4/2009 | Jaramillo et al. |
| 2009/0118716 A1 | 5/2009 | Brownell |
| 2009/0130162 A2 | 5/2009 | Pathak et al. |
| 2009/0137999 A1 | 5/2009 | Silberberg et al. |
| 2009/0164005 A1* | 6/2009 | Dove ................. A61L 27/3604 623/2.13 |
| 2009/0188900 A1 | 7/2009 | Cali et al. |
| 2009/0281530 A1 | 11/2009 | Kom |
| 2009/0326524 A1 | 12/2009 | Cali et al. |
| 2010/0011564 A1 | 1/2010 | Millwee et al. |
| 2010/0036484 A1 | 2/2010 | Hariton et al. |
| 2010/0100084 A1 | 4/2010 | Girard et al. |
| 2011/0028957 A1 | 2/2011 | Raksi et al. |
| 2011/0092966 A1 | 4/2011 | Guo et al. |
| 2011/0118609 A1 | 5/2011 | Goldshleger et al. |
| 2011/0177150 A1 | 7/2011 | Pathak et al. |
| 2011/0238167 A1 | 9/2011 | Dove et al. |
| 2011/0295363 A1 | 12/2011 | Girard et al. |
| 2012/0035720 A1 | 2/2012 | Cali et al. |
| 2012/0059487 A1 | 3/2012 | Cunanan et al. |
| 2012/0067855 A1 | 3/2012 | Guo et al. |
| 2012/0328905 A1 | 12/2012 | Guo et al. |

FOREIGN PATENT DOCUMENTS

| | | |
|---|---|---|
| GB | 2169386 A | 7/1986 |
| WO | 84/01894 A1 | 5/1984 |
| WO | 95/11047 A1 | 4/1995 |
| WO | 9518638 A1 | 7/1995 |
| WO | 95/22361 A1 | 8/1995 |
| WO | 95/34332 A1 | 12/1995 |
| WO | 96/04028 A1 | 2/1996 |
| WO | 96/13227 A1 | 5/1996 |
| WO | 1998/07452 A1 | 2/1998 |
| WO | 1998/43556 A1 | 10/1998 |
| WO | 9958082 A2 | 11/1999 |
| WO | 00/032252 A1 | 6/2000 |
| WO | 02/15948 A2 | 2/2002 |
| WO | 03/037227 A2 | 5/2003 |
| WO | 04/082536 A1 | 9/2004 |
| WO | 2006/026325 A2 | 3/2006 |
| WO | 2006/099334 A2 | 9/2006 |

OTHER PUBLICATIONS

Carpentier, A., et al., "Biological Factors Affecting Long-Term Results of Valvular Heterografts."

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Chvapil, M., et al., "Use of Chemically Purified and Cross-Linked Bovine Pericardium as a Ligament Substitute," Journal of Biomedical Materials Research, vol. 21, No. 12, pp. 1383-1394, 1987, University of Arizona Health Science Center, Tucson, AZ.

Grant, R.A., et al., "The Effects of Irradiation with High Energy Electrons on the Structure and Reactivity of Native and Cross-Linked Collagen Fibres," J. Cell Sci. vol. 7, 99. 387-405, 1970.

Fahner, P., et al., "Systematic Review of Preservation Methods and Clinical Outcome of Infrainguinal Vascular Allografts," Journal of Vascular Surgery, vol. 44, No. 3, pp. 518-524, 2006.

Fumoto, H., et al., "Performance of Bioprosthetic Valves After Glycerol Dehydration, Ethylene Oxide Sterilization, and Rehydration," Innovations, vol. 6, No. 1, Jan./ Feb. 2011.

Hauschka, P., et al., "Direct Identification of the Calcium- Binding Amino Acid, y-Carboxyglutamate, in Mineralized Tissue," Proc. Nat Acad. Sci, vol. 72, No. 10, pp. 3925-3929, Oct. 1975.

Khora, Eugene, "Methods for the Treatment of Collagenous Tissues for Bioprostheses," Biomaterials, vol. 18, Issue 2, Jan. 1997, pp. 95-105.

Jayakrishnan, A., et al., "Glutaraldehyde as a Fixative in Bioprostheses and Drug Delivery Matrices," Biomaterials, vol. 17, Issue 5, 1996, pp. 471-484.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Olde Damink, L.H.H., et al., "Influence of Ethylene Oxide Gas Treatment on the in vitro Degradation Behavior of dermal Sheep Collagen," Journal of Biomedical Materials Resarch, vol. 29, pp. 149-155, 1995.

Ohan, M., et al., "Glucose Stabilizes Collagen Sterilized with Gamma Irradiation," Wiley Periodicals, Inc., pp. 1188-1195, 2003.

R Parker, et al. Storage of Heart Valve Allografts in Glycerol With Subsequent Antibiotic Sterilisation, Thorax, 1978, 638-645, vol. 33:5, British Thoracic Society, London, UK.

Saegeman, V., et al., "Short and long term bacterial inhibiting effect of high concentrations of glycerol used in the prevention of skin allografts," Science Direct, Burns, No. 34, Mar. 2008.

Schmidt, C., et al., "Acellular Vascular Tissues: Natural Biomaterials for Tissue Repair and Tissue Engineering," Biomaterials, vol. 21, pp. 2215-2231, 2000.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

Al-Fagih, M.R., et al., "Aortic Valve Repair Using Bovine Pericardium for Cusp Extension," Journal of Thoracic and cardiovascular Surgery, vol. 9, No. 5, pp. 760-764, 1988.

* cited by examiner

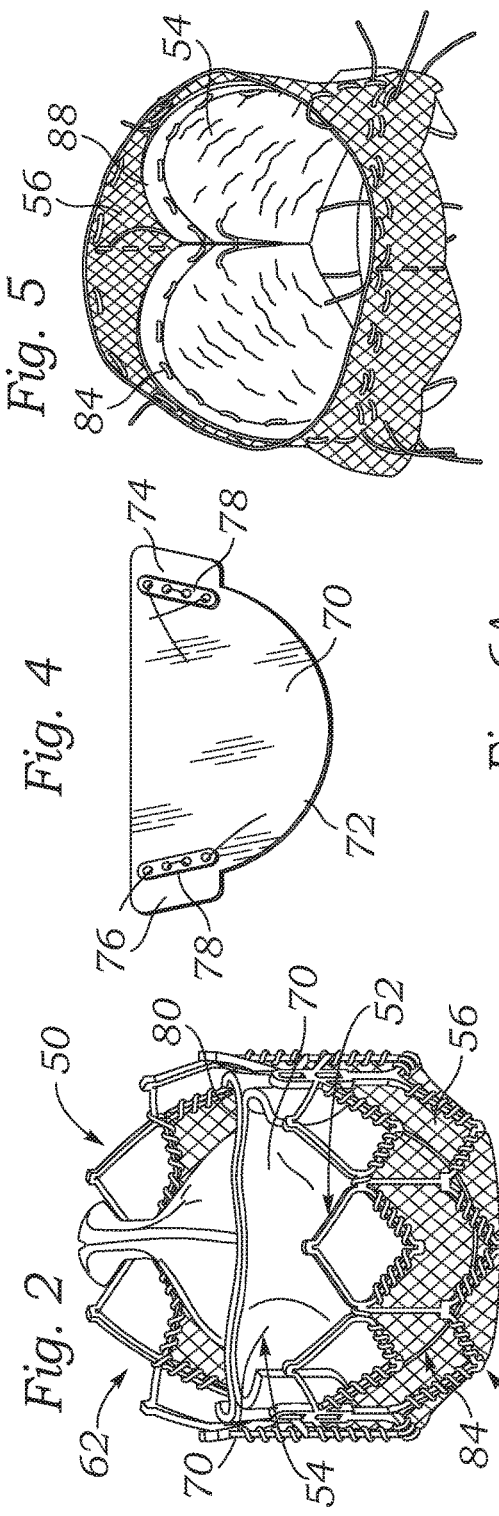
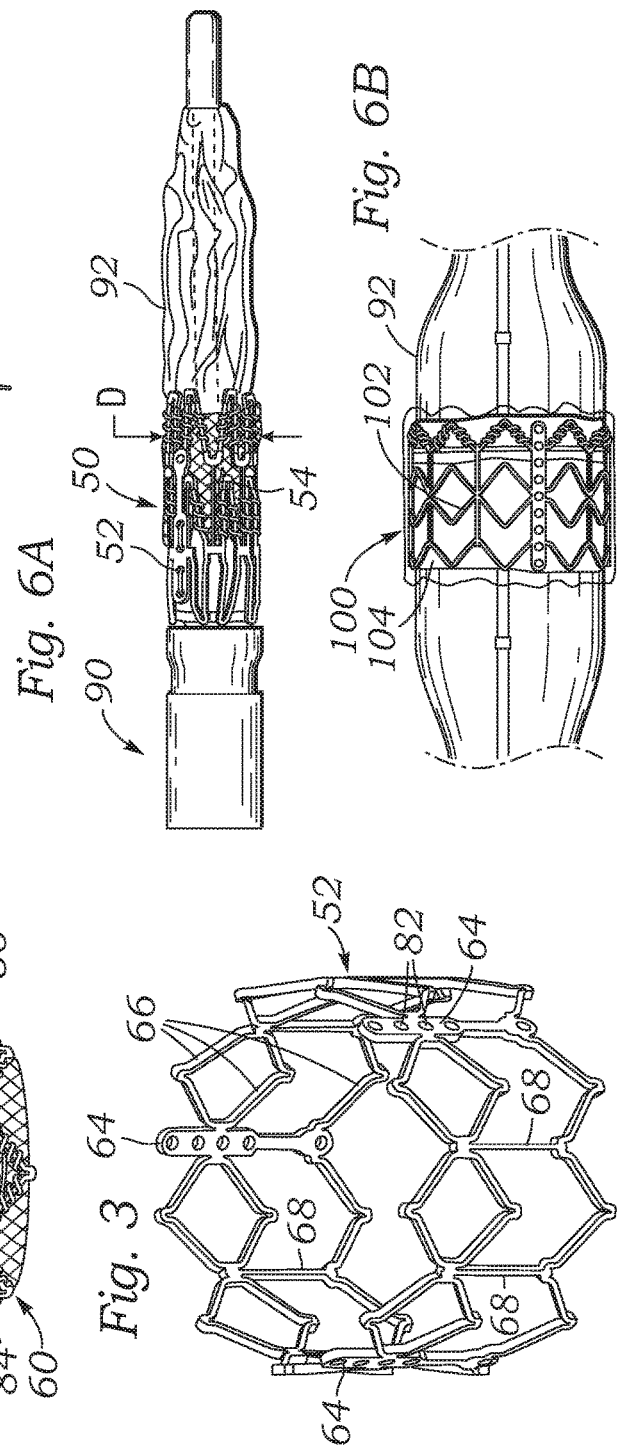
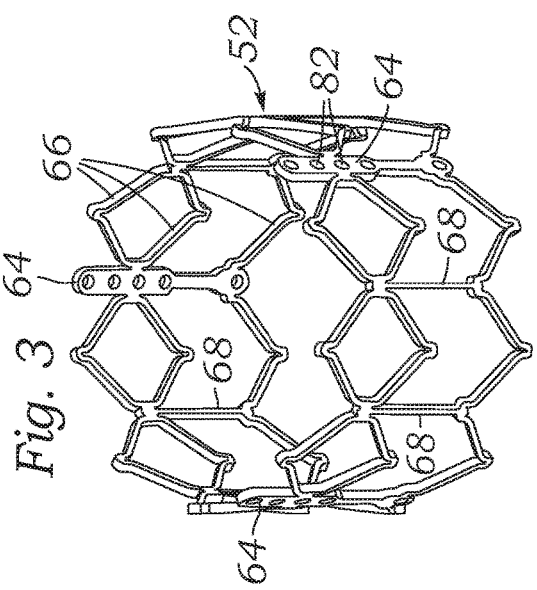

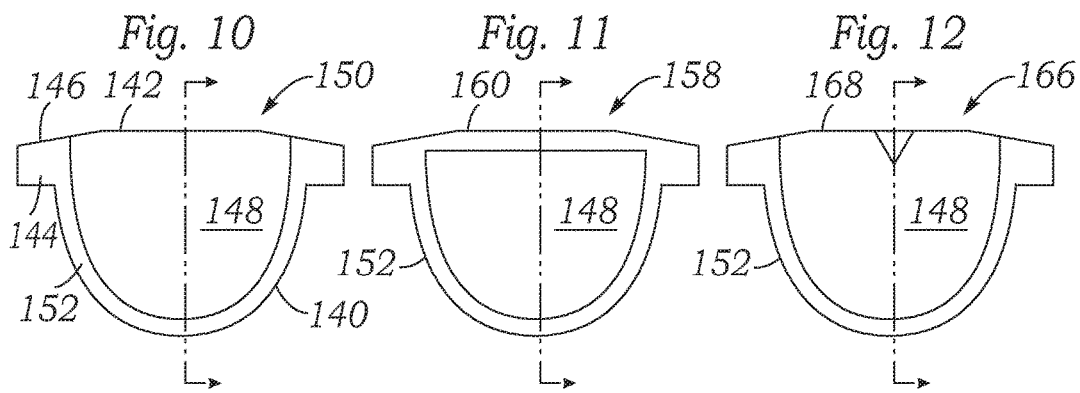
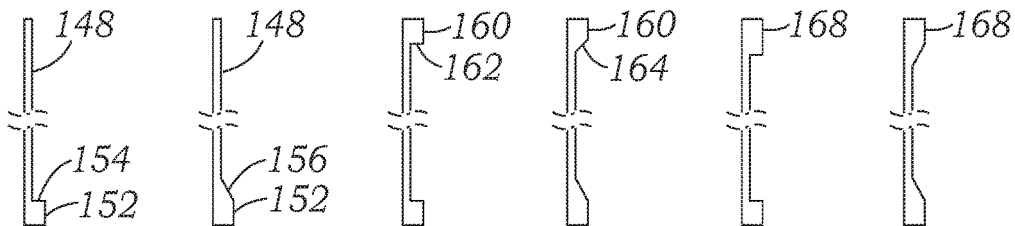
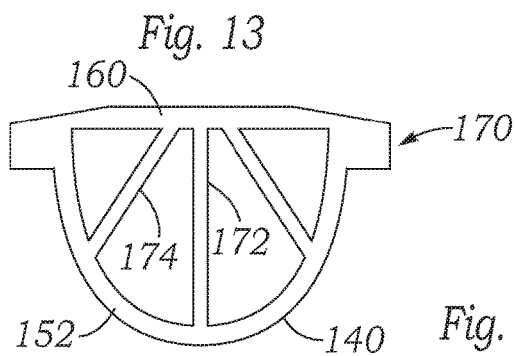
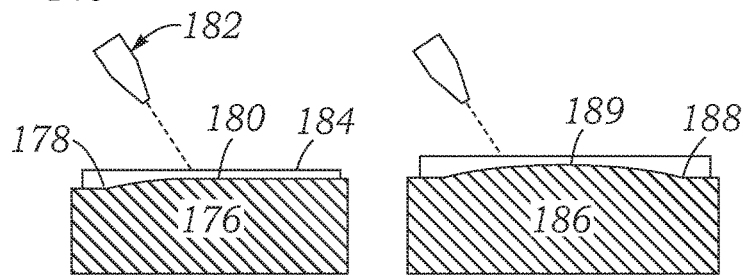

METHODS OF CONDITIONING SHEET BIOPROSTHETIC TISSUE

CROSS REFERENCE TO RELATED APPLICATIONS

This application is a continuation of U.S. patent application Ser. No. 13/950,154, filed Jul. 24, 2013, now U.S. Pat. No. 9,498,288, which is a continuation of U.S. patent application Ser. No. 13/069,827, filed Mar. 23, 2011, now U.S. Pat. No. 8,846,390, which claims the benefit of U.S. Patent Application No. 61/316,801 filed on Mar. 23, 2010, and of U.S. Patent Application No. 61/381,858 filed on Sep. 10, 2010, the entire disclosures of which are incorporated by reference.

FIELD OF THE INVENTION

The field of the present invention is the conditioning of bioprosthetic tissues for use in implants and, more particularly, for methods for smoothing and thinning sheet bioprosthetic tissue for use in prosthetic heart valves.

BACKGROUND OF THE INVENTION

Medical technology has long been capable of replacing damaged or diseased heart valves through open heart surgery. Such valves have included mechanical devices as well as those using biological material from humans (homograft tissue) and animals (xenograft tissue). The two primary types of prosthetic heart valves known in the art are mechanical valves and bioprosthetic valves. Bioprosthetic valves may be formed from an intact, multi-leaflet porcine (pig) heart valve, or by shaping a plurality of individual flexible leaflets out of bovine pericardial tissue or other materials, and combining the leaflets to form the valve. One advantage of bioprosthetic valves, unlike mechanical valves, is that the patient receiving the valve typically does not require long term treatment with anticoagulants.

The pericardium is a sac around the heart of vertebrate animals which contains lubricating fluid, and bovine (cow) pericardium is commonly used to make individual leaflets for prosthetic heart valves. The bovine pericardium is first harvested from the animal and then chemically fixed to crosslink collagen and elastin molecules in the tissue and increase the tissue durability, before being cut into leaflets.

A good discussion of the various physical properties of fixed bovine pericardium is given in Simionescu, et al., Mapping of Glutaraldehyde-Treated Bovine Pericardium and Tissue Selection For Bio-prosthetic Heart Valves, Journal of Bio-Medical Materials Research, Vol. 27, 697-704, John Wiley & Sons, Inc., 1993. Simionescu, et al., recognized the sometimes striking variations in physical properties of the pericardial tissue, even in the same pericardial sac.

The pericardial sac consists of two distinct elements of tissue. The visceral or serous layer is of very thin translucent tissue most adjacent the heart which is not used to construct artificial heart valve leaflets. This inner layer of the pericardium is conical and surrounds the heart and the roots of the great blood vessels. The parietal pericardial membrane is a thicker membrane of multi-layered connective tissue covered with adipose tissue. The outside fat/adipose tissue is removed (e.g., peeled off) when harvested. The remaining multi-layered fibrous tissue primarily contains collagen fibers with a generally fibrous outer surface and a smooth inner surface. This remaining membrane is used for making the leaflets for artificial heart valves.

A number of steps in a typical commercial process for preparing pericardial tissue for heart valve leaflets are illustrated in FIG. 1. First, a fresh pericardial sac 20 is obtained from a regulation slaughterhouse. The sac 20 is then cut open along predetermined anatomical landmarks, as indicated at 22. The sac is then flattened at 24 and typically cleaned of excess fat and other impurities. After trimming obviously unusable areas, a window 26 of tissue is fixed, typically by immersing in an aldehyde to cross-link the tissue, and then quarantined for a period of about two weeks. Normally, two windows of 4 to 6 inches on a side can be obtained from one bovine pericardial sac. Rough edges of the tissue window 26 are removed and the tissue bio-sorted to result in a tissue section 28. The process of bio-sorting involves visually inspecting the window 26 for unusable areas, and trimming the section 28 therefrom. Subsequently, the section 28 is further cleaned as indicated at 30.

The section 28 is then placed flat on a platform 32 for thickness measurement using a contact indicator 34. The thickness is measured by moving the section 28 randomly around the platform 32 while a spindle 36 of the indicator 34 moves up-and-down at various points. The thickness at each point is displayed at 38 and recorded by the operator. After sorting the measured sections 28 by thickness, as indicated at 40, leaflets 42 are die cut from the sections, with thinner leaflets 42 generally being used for smaller valves, and thicker leaflets being used for larger valves. Of course, this process is relatively time-consuming and the quality of the final leaflets is dependent at several steps on the skill of the technician. Moreover, the number of leaflets obtained from each sac is inconsistent, and subject to some inefficiency from the manual selection process. One solution to this time-consuming manual process is provided in U.S. Pat. No. 6,378,221 to Ekholm, et al., in which a three-axis programmable controller manipulates a pericardial sheet with respect to a thickness measurement head to topographically map the sheet into similar thickness zones for later use. However, even with advanced methods the variability of the bovine pericardium results in an extremely low yield of sheet usable for heart valve leaflets; averaging less than 2 sheets per sac.

Typically, harvested bovine pericardial tissue ranges in thickness from 250 microns up to 700 microns, though most of the material is between 300-700 microns thick.

Valves using flexible leaflets, such as those made of bovine pericardial tissue, have acquired increased significance of late because these valves may be implanted by other than open heart surgery. The valves are constructed using radially expandable stents with flexible (e.g., pericardial) leaflets attached. Implant methods include compressing the valve radially by a significant amount to reduce its diameter or delivery profile, inserting the valve into a delivery tool, such as a catheter or cannula, and advancing the delivery tool to the correct anatomical position in the heart. Once properly positioned, the valve is deployed by radial expansion within the native valve annulus, either through self-expanding stent structure or with an expansion balloon. The collapsed valve in the catheter may be introduced through the vasculature, such as through the femoral artery, or more directly through an intercostal incision in the chest. The procedure can be accomplished without open heart surgery and possibly without stopping the heart during the procedure.

One example of percutaneous heart valve delivery is U.S. Pat. No. 6,908,481 to Cribier and Edwards Lifesciences of Irvine, Calif., which shows a valve prosthesis with an expandable frame on which a collapsible valvular structure is mounted. Another compressible/expandable heart valve is shown in U.S. Patent Publication No. 2010/0036484, also from Edwards Lifesciences. Further examples of such methods and devices are disclosed in U.S. Pat. No. 7,621,948 and US Patent Publication No. 2006/0259136, and the number of other configurations of such valves is exploding as the promise of the technology grows. The disclosures of each of these references are incorporated herein by reference.

These new devices require thinner components that enable crimping of the valve down to a size that can pass through the delivery tool. One limiting component is the thickness of the bioprosthetic tissue. As mentioned, pericardial layers range from 250-700 microns, but only a small percentage of the harvested pericardium falls close to the low end, which is the most useful for compressible/expandable valves.

U.S. Pat. No. 7,141,064 proposes compressing bovine pericardium to reduce its thickness by about 50 percent for use in heart valve leaflets. The compression may also smooth out the tissue surface to reduce thickness non-uniformity.

Despite much research into various bioprosthetic tissue, in particular for heart valve leaflets, there remains a need for thinner and more consistent thickness tissues for use in fabricating smaller delivery profile bioprostheses.

SUMMARY OF THE INVENTION

The present invention is directed to the preparation of bioprosthetic material for cardio implantation. Bovine pericardial membrane having a fibrous surface and a smooth surface are selected. This preparation can increase the yield of cardio valve leaflets from pericardial membrane and can eliminate thrombogenic agents such as dangling fibers.

In accordance with one aspect, a method for preparing bioprosthetic tissue membrane material includes first selecting a tissue membrane (e.g., bovine pericardial membrane) having a fibrous side and a smooth side. Material is then removed from the fibrous side of the selected membrane to reduce the thickness of the membrane and smooth the fibrous side. The material may be removed by shearing with a mechanical device, such as a dermatome or vibratome. Alternatively, the material may be removed by ablation with a laser.

In the just-described method, the selected membrane may be conditioned by compressing the selected tissue membrane and cross-linking the material of the membrane while under compression. Furthermore, the method may involve treating the membrane reduced in thickness by capping of calcification nucleation sites and/or by borohydride reduction. In accordance with one aspect, the method further comprises at least partially fixing the selected membrane prior to the removing step.

In accordance with another method disclosed herein, bioprosthetic tissue membrane material is prepared by first selecting a tissue membrane having a fibrous side and a smooth side, conditioning the selected tissue membrane by compression and cross-linking the membrane while under compression, and then removing conditioned material from the fibrous side of the selected tissue membrane to reduce the thickness of the membrane and smooth the fibrous side. The tissue membrane maybe pericardial membrane, such as bovine or equine. The method may involve treating the membrane reduced in thickness by capping and/or by borohydride reduction. In accordance with one aspect, the step of removing is accomplished by shearing with a mechanical device, such as a dermatome or vibratome. Or, the step of removing is accomplished by ablating the conditioned material with a laser.

In accordance with a still further aspect, a method for preparing bioprosthetic tissue membrane material comprises first selecting a tissue membrane having a fibrous side and a smooth side. The material of the membrane is the least partially cross-linked, and then infused with a second cross-linking material of a chain length to allow spending of large inter-fibril domains. Subsequently, the tissue membrane is the least partially compressed. The tissue membrane may be bovine pericardial membrane. The method may also involve lightly compressing the selected membrane prior to at least partially cross-linking the membrane. The method may include treating the membrane reduced in thickness by capping and/or by borohydride reduction. In accordance with one aspect, material is removed from the fibrous side of the lightly compressed tissue membrane.

Another aspect of the present application is a heart valve comprising a plurality of leaflets each made of sheet tissue having a first region with a uniform first thickness and a second region with a uniform second thickness greater than the first thickness. The leaflets preferably each have a cusp edge opposite a free edge, and the second region extends in a generally uniform width strip along the cusp edge. The second region also may extend in a generally uniform width strip along the free edge of each leaflet. Furthermore, the second region may extend in generally uniform width strips radially from the center of the free edge to the cusp edge. Desirably, transitions between the thicknesses of the first and second regions is gradual. In one embodiment, the heart valve includes a support frame to which peripheral edges of the leaflets attach with sutures, and the second region extends along the leaflet edges through which sutures are passed.

In a first separate aspect of the invention, a dermatome is employed with the fibrous surface of the membrane and moved relative thereto to smooth the surface and/or reduce the thickness of the membrane to a specific uniform thickness, for instance no more than 250 microns. The dermatome is constrained by spacers to control the thickness of the membrane remaining with the shaved material removed.

In a second separate aspect of the invention, the fibrous surface of the membrane is removed to smooth the surface and/or reduce the thickness of the membrane to a specific uniform thickness. The membrane is first subjected to light compression and cross-linking to smooth the fibrous surface and improve the material for ablation.

In a third separate aspect of the invention, a laser is directed at the fibrous surface of the membrane and moved relative thereto to ablate the surface to smooth the surface and/or reduce the thickness of the membrane to a specific uniform thickness. The wavelength, power and pulse rate of the laser are selected which will smooth the fibrous surface as well as ablate the surface to the appropriate thickness. The membrane may first be subjected to light compression and cross-linking to smooth the fibrous surface and improve the material for ablation.

In a fourth separate aspect of the present invention, the selected bovine pericardial membrane is first at least partially cross-linked, then infused with a second cross-linking material of a chain length to allow spanning of large inter-fibril domains. The membrane is then compressed, and may then be treated by capping and borohydride reduction.

In a fifth separate aspect of the present invention, any of the foregoing processes may be used in combination to greater advantage.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 2 is a perspective view of a representative embodiment of a prosthetic heart valve that may be made with tissue conditioned in accordance with the present application;

FIG. 3 is a perspective view of a support frame that can be used in the prosthetic valve of FIG. 2;

FIG. 4 is a flattened view of a leaflet of the valve shown in FIG. 2;

FIG. 5 is a bottom perspective view of a valve leaflet structure connected to a reinforcing skirt so as to form a leaflet assembly;

FIG. 6A depicts a side view of an exemplary prosthetic heart valve crimped on a balloon delivery catheter;

FIG. 6B shows the prosthetic valve of FIG. 6A mounted on the balloon delivery catheter and in its expanded state;

FIG. 10 is a plan view of a prosthetic heart valve leaflet having a thickened peripheral edge in areas where sutures penetrate for attachment to a structural stent;

FIGS. 10A and 10B are sectional views through a radial midline of the leaflet of FIG. 10 showing two different thickness profiles;

FIG. 11 is a plan view of a prosthetic heart valve leaflet having a thickened peripheral edge in areas where sutures penetrate for attachment to a structural stent as well as a thickened free edge to reduce the risk of elongation at that location;

FIGS. 11A and 11B are sectional views through a radial midline of the leaflet of FIG. 11 showing two different thickness profiles;

FIG. 12 is a plan view of a prosthetic heart valve leaflet having a thickened peripheral edge in areas where sutures penetrate for attachment to a structural stent as well as a thickened triple point area in the free edge simulating nodules of Arantius;

FIGS. 12A and 12B are sectional views through a radial midline of the leaflet of FIG. 12 showing two different thickness profiles;

FIG. 13 illustrates in plan view an alternative leaflet having a thickened peripheral edge region, a thickened strip along the free edge, and a plurality of thickened radial strips extending from the free edge to the cusp edge;

FIGS. 14A and 14B are schematic views of exemplary leaflet skiving processes utilizing contoured forming molds;

FIG. 15A is a schematic view of a dermatome cutting tissue, while

DETAILED DESCRIPTION OF THE PREFERRED EMBODIMENTS

Figure 1:
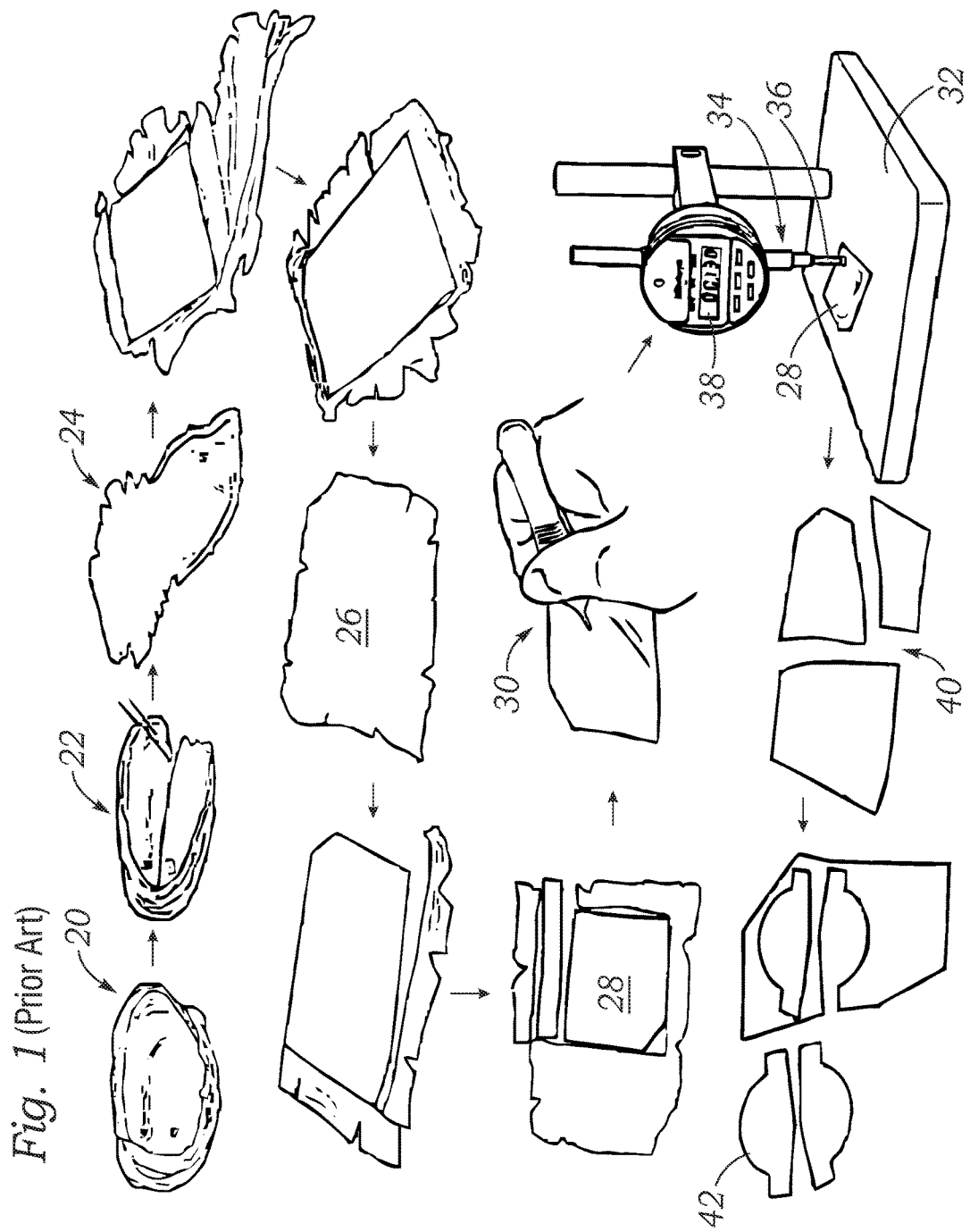
FIG. 1 illustrates a sequence of prior art steps for preparing and measuring the thickness of bovine pericardial tissue prior to forming leaflets from the tissue.

In the primary embodiment, the preparation of leaflets for prosthetic heart valves, in particular expandable heart valves, is described. The leaflets are desirably incorporated in expandable prosthetic heart valves that are initially crimped (or even rolled) into a small delivery profile or diameter to be passed through a catheter or other delivery system and then expanded at the implantation site, typically a valve annulus. The heart valves comprise structural stent bodies with a plurality of flexible leaflets incorporated therein. Various materials are suitable for the stent body, although certain nickel-titanium alloys (i.e., Nitinol) are preferred for their super-elasticity and biocompatibility. It should also be noted that specific stent body configurations are not to be considered limiting, and various construction details may be modified.

Although forming prosthetic heart valve leaflets to be thinner helps reduce the delivery size of expandable valves, forming thinner leaflets as well as conditioning the leaflets as described herein is believed to be advantageous for conventional heart valves as well. For example, smoothing the rough surface of pericardial tissue is believed to improve durability of the leaflets by reducing loose fibers and attendant thrombogenicity.

Heart valves with durability in excess of 10 years have had bovine pericardial leaflet thicknesses ranging from 0.014-0.023 inches (~350-580 microns), with smaller valves utilizing thinner leaflets and larger valves having thicker leaflets. Current percutaneous valves may employ porcine pericardial tissue with thicknesses down to 0.004-0.005 inches (~100-130 microns). Although naturally-occurring porcine tissue is somewhat thinner than naturally occurring pericardial tissue, there are certain advantages to using pericardial leaflets.

Various tissues may be used for the leaflets, though a preferred tissue for use in the primary application of heart valve leaflets is bovine parietal pericardial membrane. Though the thickness and strength of bovine pericardial tissue is considered desirable for longer lasting valves, other bioprosthetic tissue such as porcine, equine and other mammalian pericardium, including human, may be used. Furthermore, tissue from other anatomical sources may be used, such as dura mater, peritoneum, diaphragm, or others. Any tissue membrane that has a suitable durability and elasticity as pericardium is a candidate, though those of skill in the art will appreciate that certain materials may be better suited for any one specific application. In general, tissues that contain fibrous collagen, in particular classed as Type I or Type III collagen, and elastic fibers or elastin may be suitable for use in fabricating heart valve leaflets. Other potential types of collagen that can be used are hybrid natural collagen solution or electrospun collagen elastin fabric. Also, certain so-called engineered tissue may be used, which are synthesized by growing collagenous tissue over a typically mesh frame or scaffold. These source are collectively referred to as "tissue membranes," and may all benefit from the principles described herein, though some like bovine pericardium is especially well-suited for conditioning heart valve leaflets in accordance with the present application.

As mentioned above, the pericardial sac consists of two or more distinct layers, one side being relatively smooth while the opposite surface comprises connective tissue covered with adipose tissue, some of which is peeled off when harvested, and is thus fibrous. The methods described herein are particularly useful for smoothing out the fibrous side to form a consistently thick and smooth membrane. In some cases, the thickness of the fibrous adipose tissue side may also be reduced to produce a uniformly thin membrane, preferably below 300 microns for use in collapsible/expandable valves.

With reference to FIG. 2, an exemplary one-piece prosthetic heart valve 50 is shown that can utilize a bovine membrane of uniform thickness. The valve 50 will be described in some detail to illustrate some of the benefits of the leaflet fabrication methods described herein, but more specifics on the valve structure may be found in U.S. Patent Publication No. 2010/0036484, filed Jun. 8, 2009, entitled "LOW PROFILE TRANSCATHETER HEART VALVE," and assigned to Edwards Lifesciences, the disclosure of which is incorporated herein by reference. Alternatively, another minimally-invasive valve that may utilize thin pericardial membrane is found in U.S. Pat. No. 6,733,525, issued May 11, 2004, entitled "ROLLED MINIMALLY INVASIVE HEART VALVES AND METHODS OF USE," which disclosure is expressly incorporated herein by reference.

Valve 50 in the illustrated embodiment generally comprises a structural frame, or stent 52, a flexible leaflet structure 54 supported by the frame, and a flexible skirt 56 secured to the outer surface of the leaflet structure. The illustrated valve 50 may be implanted in the annulus of the native aortic valve, but also can be adapted to be implanted in other native valves of the heart or in various other ducts or orifices of the body. Valve 50 has a "lower" or inflow end 60 and an "upper" or outflow end 62. Blood flows upward freely through the valve 50, but the flexible leaflet structure 54 closes to prevent reverse downward flow. The flexible leaflet structure 54 thus provides flexible fluid occluding surfaces to enable one-way blood flow.

Valve 50 and frame 52 are configured to be radially collapsible to a collapsed or crimped state for introduction into the body on a delivery catheter and radially expandable to an expanded state for implanting the valve at a desired location in the body (e.g., the native aortic valve). Frame 52 can be made of a plastically-expandable material that permits crimping of the valve to a smaller profile for delivery and expansion of the valve using an expansion device such as the balloon of a balloon catheter. Exemplary plastically-expandable materials include, without limitation, stainless steel, a nickel based alloy (e.g., a nickel-cobalt-chromium alloy), polymers, or combinations thereof. Alternatively, valve 50 can be a so-called self-expanding valve wherein the frame is made of a self-expanding material such as Nitinol. A self-expanding valve can be crimped and held in the collapsed state with a restraining device such as a sheath covering the valve. When the valve is positioned at or near the target site, the restraining device is removed to allow the valve to self-expand to its expanded, functional size.

Referring also to FIG. 3 (which shows the frame alone for purposes of illustration), the frame 52 is a generally tubular, stent-like structure having a plurality of angularly spaced, vertically extending struts, or commissure attachment posts 64. The reader will note that the posts 64 in FIG. 3 are somewhat modified from those shown in FIG. 2, the differences being minimal. The posts 64 are interconnected via several rows of circumferentially extending struts 66. Thinner vertical (axial) struts 68 intermediate the commissure attachment posts 64 connect to and extend between adjacent horizontal rows of struts 66. The struts in each row are desirably arranged in a zigzag or generally saw-tooth pattern extending in the direction of the circumference of the frame as shown. Adjacent struts in the same row can be interconnected to one another as shown to form an angle when expanded, desirably between about 90 and 110 degrees. This optimizes the radial strength of frame 52 when expanded yet still permits the frame 52 to be evenly crimped and then expanded in the manner described below.

Leaflet structure 54 desirably comprises three separate connected leaflets 70 such as shown in FIG. 4, which can be arranged to collapse in a tricuspid arrangement, as best shown in FIGS. 2 and 5. Each leaflet 70 has a curved lower cusp edge 72 opposite a generally straight upper free edge 74, and two commissure flaps 76 extending between the free edge 74 and the lower edge 72. The curved cusp edge 72 forms a single scallop in the leaflet structure 54. When secured to two other leaflets 70 to form the leaflet structure 54, the curved cusp edges 72 of the leaflets collectively form a scallop-shaped lower edge of the leaflet structure (as best shown in FIG. 5). As further shown in FIG. 4, two reinforcing bars 78 can be secured to each leaflet 70 adjacent to flaps 76 (e.g., using sutures). The flaps can then be folded over bars 78 and secured in the folded position using sutures. If desired, each bar 78 can be placed in a protective sleeve (e.g., a PET sleeve) before being secured to a leaflet.

Leaflets 70 attach to one another at their adjacent sides to form commissures 80 of the leaflet structure (see FIG. 2 at the edges where the leaflets come together). Leaflet structure 54 can be secured to frame 52 using various techniques and mechanisms. For example, as best shown in FIG. 2, commissures 80 of the leaflet structure desirably are aligned with the support posts 64 and secured thereto using sutures through holes 82 (FIG. 3). The point of attachment of the leaflets to the posts 64 can be reinforced with the bars 78 (FIG. 4), which desirably are made of a relatively rigid material (compared to the leaflets), such as stainless steel.

As mentioned, the lower edge of leaflet structure 54 desirably has an undulating, curved scalloped shape. A suture line 84 visible on the exterior of the skirt 56 in FIG. 2 tracks the scalloped shape of the leaflet structure 54. By forming the leaflets with this scalloped geometry, stresses on the leaflets are reduced, which in turn improves durability of the valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the valve.

Referring again to FIGS. 2 and 5, the skirt 56 can be formed, for example, of polyethylene terephthalate (PET) ribbon. The leaflet structure 54 attaches to the skirt via a thin PET reinforcing strip 88 (or sleeve), FIG. 5, which enables a secure suturing and protects the pericardial tissue of the leaflet structure from tears. The leaflet structure 54 is sandwiched between skirt 56 and the reinforcing strip 88. The suture 84, which secures the reinforcing strip and the leaflet structure 54 to skirt 56 can be any suitable suture, and desirably tracks the curvature of the bottom edge of leaflet structure 54, as see on the exterior of the skirt 56 in FIG. 2. The skirt 56 and leaflet structure 54 assembly resides inside of frame 52 and secures to the horizontal struts 66 via a series of zigzag pattern sutures 86, as shown in FIG. 2.

To assemble, the heart valve leaflets 70 are cut from a membrane such as bovine pericardium and thinned, conditioned or otherwise shaped in accordance with the principles described herein. In the expandable valve 50 described above, the leaflets 70 attach within the tubular stent fame 52 and the three adjacent pairs of free edges 74 meet in the middle of the valve at coapting lines oriented equiangularly with respect to one another. The free edges 74 billow inward to meet along the coapting lines. The assembled valve is then stored in a sterile fluid, typically glutaraldehyde, for a period prior to implantation.

FIG. 6A shows the prosthetic heart valve 50 crimped onto balloon 92 of a balloon delivery catheter 90. As explained herein, the thinning of the bioprosthetic tissue applied to the material for the leaflets helps enable the outer diameter D of the assembled valve and balloon catheter to be as small as 6 mm. Expanded prosthetic heart valve sizes are typically anywhere between 20 mm up to about 30 mm.

FIG. 6B shows an alternative embodiment of a prosthetic valve 100 comprising a frame 102 and a leaflet structure 104 mounted to the inside of the frame (e.g., using sutures as shown and described above). The valve 100 is shown in its expanded state after the expansion balloon 92 has been inflated. The size of the expanded valve 100 varies depending on the patient, typically between 22 and 40 mm.

Implant methods include compressing the valve 50 radially by a significant amount to reduce its diameter or delivery profile, inserting the valve into a delivery tool, such as a catheter or cannula, and advancing the delivery tool to the correct anatomical position in the heart. Once properly positioned, the valve 50 is deployed by radial expansion within the native valve annulus with the expansion balloon 92. The collapsed valve 50 in the catheter may be introduced through the vasculature, such as through the femoral artery, or more directly through an intercostal incision in the chest. It is important for the valve to be as small as possible. A large valve requires a large diameter catheter, which is difficult to push through the femoral artery, for example. To enable smaller constricted heart valves, the maker thins the tissue used to make the leaflets 70. Preferably the conditioning includes reducing the tissue thickness, but may also involve smoothing the tissue to result in a thin, constant-thickness membrane from which to cut leaflets. Or, the leaflets may be formed first and then thinned. There are a number of ways to thin the tissue including using laser ablation, as explained below.

It should again be noted that the thinned pericardial membrane described herein may be used in various types of heart valves, including conventional surgical valves. The method can also be used to merely smooth out or "heal" the tissue surface to eliminate thrombogenic agents such as dangling fibers, without any appreciable thinning Such smoothed tissue which remains relatively thick may be used in conventional surgical heart valves. One specific example, of conventional heart valves that may utilize tissue in accordance with the present invention is the Carpentier-Edwards® PERIMOUNT® line of Pericardial Bioprostheses, available from Edwards Lifesciences. The basic construction of the PERIMOUNT® valve is seen in U.S. Pat. No. 5,928,281, which disclosure is expressly incorporated herein by reference.

Desirably, pericardial layers used for transcatheter heart valve leaflets are in the 250-500 micron range, and preferably closer to 250 microns. Unfortunately, only a small percentage of the harvested pericardium falls close to the 250 micron thickness. Most of the material is 300-700 microns. As a result, each pericardial sac only yields about 1-2 leaflets suitable for THV. However, the pericardial tissue used for building heart valves consists of multiple layers of tissue with similar components and the majority of the collagen fibers are parallel between layers. This unique structure has made it possible to use various means, e.g., lasers, razors, to remove some of the tissue. The tissue removed desirably comes from the fibrous side from which the adipose tissue was previously removed. This creates a more defined thinner pericardial membrane with a more appropriate low profile.

With the advent of laser technology, ablation of corneal tissue has become common. Excimer lasers have been used for such procedures. Reference is made to U.S. Pat. No. 4,840,175. Recent work with mode locking lasers with very short pulse lengths in Picosecond and Femtosecond ranges have also been considered to reduce heating. Lasers have also been used for cutting tissue, for ablation of heart muscle to treat arrhythmia and for dental applications. Two other disclosures of the use of lasers for tissue removal on humans are in U.S. Pat. No. 7,022,119 to Holha and U.S. Pat. No. 7,367,969 to Stoltz, et al. These laser references are incorporated herein by reference. Laser ablation using the laser assisted in situ keratomileusis process has also been suggested to reduce the thickness of bovine pericardium to create membrane tissue for a wide variety of uses including heart valves in U.S. Patent Publication No. 2007/0254005, the disclosure of which is incorporated herein by reference.

Figure 7:
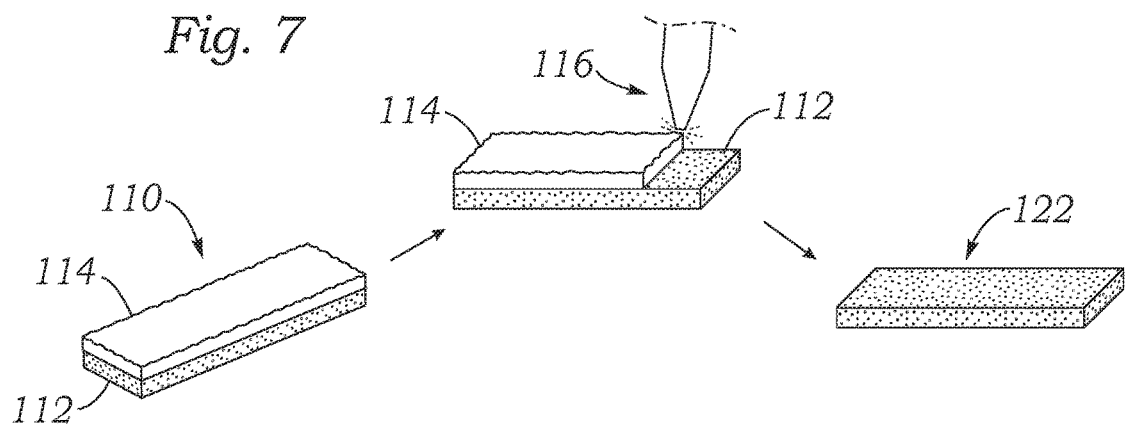
FIG. 7 is a schematic view of a sequence of tissue conditioning of pericardial membrane with laser ablation.

FIG. 7 schematically shows a sequence of events in ablating bioprosthetic tissue in preparation for making implant components, such as heart valve leaflets. To prepare the pericardial material for cardio implantation, a membrane 110 of bovine pericardial membrane with the bulk of the outside fat/adipose tissue removed is selected having a thickness of 250 microns or more (typically in the range of 300-700 microns). The collagenous layer 112 shown on the underside which makes up the inner surface of the pericardial sac in vivo still has some of the outside fat/adipose tissue 114 attached thereto.

Tissue ablation may be accomplished with the membrane 110 exposed, for example, in planar form, as indicated by the flow chart of FIG. 7. In a planar configuration, the membrane 110 is fixed or held in an appropriate plane. A laser 116 is directed at the upper fibrous surface 114 of the membrane 110 with a focal point adjusted for ablation at or near the top of the collagenous layer 112. Alternatively, although not shown, the membrane 110 could be positioned on a rotating mandrel so that an adjacent laser may remove tissue. Other physical configurations for creating relative tissue/laser movement are contemplated. Relative movement between the laser 116 and the surface 114 is then effected to ablate material from the membrane 110. Depending on the degree of transparency of the membrane tissue to the laser beam, more than one pass may be needed to achieve the desired uniform thickness.

The specification for a laser found to be useful in the ablation of pericardium for creating heart valve leaflets includes: a dual axis scanning lens; 2× beam expansion; 1550 nm wave length; 31.5 gJ pulse energy on target; 1.6 W average power; 50 Hz repetition rate; 650 fs pulse width (ref); 30 μm laser spot size; elliptical polarization; 112 mm focal length; 400 mm/s coarse milling speed (20 μm fill spacing in cross hatch pattern); and 800 mm/s fine milling speed (20 μm fill spacing in cross hatch pattern).

A substantial amount of technology has been developed for guiding lasers and ablating tissue with great precision. Corneal ablation has been widely practiced for almost two decades. This technology using excimer lasers has become common. Reference is made again to U.S. Pat. No. 4,840,175, the disclosure of which is incorporated herein by reference. Recent work with mode locking lasers having very short pulse lengths in Picosecond and Femtosecond ranges with reduce heating has also been studied.

Milling machines for such precise work not on a patient are also available. Milling machines employing a laser having the above specifications as the operative tool found to be useful for conveniently processing pericardium membranes have a 2-axis scanning laser head, tissue holders to facilitate loading the work into the machine, an X-Y table to increase working area of the laser and an automatic tissue holder loading mechanism. Mechanisms as described can be employed to selectively ablate a mounted pericardium membrane to generate patterns of different thicknesses as discussed below.

The operation of the milling machine is automated according to input data defining the pattern and the coarseness of the cut. Typically such machines are arranged to control the depth of cut based on the specific height of the surface being cut. With such an arrangement, the resulting surface will reflect the precut contour. To avoid this result, a fixed reference may be used rather than the height of the surface being cut. In this way, the entire pattern on the work will lie in a plane with each completed cut. Multiple cuts then are used to reach the desired membrane thickness.

To retain the appropriate longevity of pericardial membrane leaflets and achieve a sufficiently compact package to be inserted into position through the femoral artery, a specific tissue thickness of the leaflets is required. For instance, a uniform thickness of 250 microns has been found particularly useful, though uniform thicknesses between 250-500 microns may be suitable. The wavelength, power and pulse rate of the laser 116, 120 are selected which will smooth the fibrous surface to eliminate thrombogenic agents as well as ablate the surface to the appropriate thickness. Various wavelengths may be appropriate for this process without generating excess heat while also being efficient. If ultra-short-pulsed lasers are used, it is believed that the laser wavelength does not significantly change the result. Leaflet samples have been made utilizing a 1550 nm wavelength.

This preparation can increase the yield of cardio valve leaflets from pericardial membrane. Indeed, it is expected that at least 5 heart valve leaflets may be obtained per pericardial sac using the methods disclosed herein.

Laser ablation of pericardium is understood to be advantaged if performed on dry tissue. This may be accomplished by first fixing the specimen 110 with a glycerin-based treatment using glutaraldehyde or equivalent and drying the tissue prior to laser ablation. Such a glycerin-based drying process is disclosed in U.S. Patent Publication No. 2008/0102,439, published May 1, 2008, to Tian et al., the disclosure of which is incorporated herein by reference.

Figure 8:
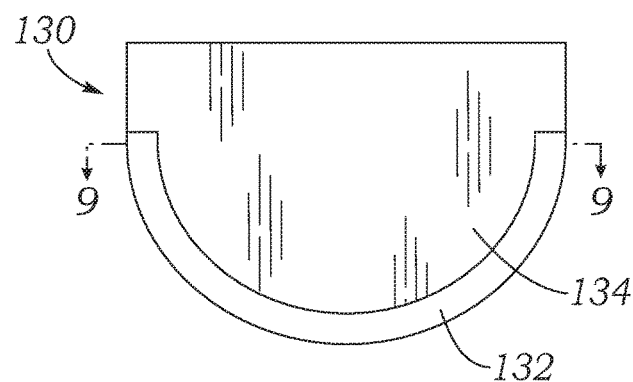
FIG. 8 is a flattened plan view of a valve leaflet showing a reinforcing region formed by uniformly thick tissue adjacent the bottom edge of the leaflet.

In addition to producing a single uniform thickness, the methods described herein also may be used to selectively thin the tissue to obtain regions of uniform but different thicknesses. One particularly useful example is shown in FIG. 8, which shows a heart valve leaflet 130 having a peripheral region 132 that is thicker than the rest of the leaflet 134. In particular, the lower curved or cusp edge of the leaflet can be thickened for later securement to the skirt 56 described above. The thickened region 132 desirably includes a generally uniform width strip. This is similar to securing a reinforcing strip 88 as described above, and both techniques may be used for even greater reinforcement. Three such leaflets 130 can be prepared in the same manner and then connected to each other at their commissure edges in a tricuspid arrangement to form a leaflet structure, such as shown at 54 in FIGS. 2 and 5. The reinforcing regions 132 on the leaflets collectively define a ribbon or sleeve that extends along the lower edge portion of the inside surface of the leaflet structure 54.

Figure 9:
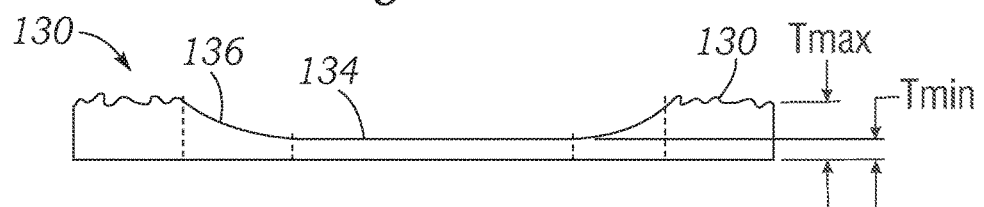
FIG. 9 is an edge view of a valve leaflet showing a reinforcing region.

FIG. 9 illustrates an edge view of the leaflet 130 with a stress relieved profile, having the reinforcing regions 132 transition slowly in thickness as seen at ramps 136 to the thinner main portion 134 of the leaflet 130. The reinforcing regions 132 are illustrated somewhat rough to simulate microscopic tissue irregularities, though the same surface may be made smoother using certain techniques described herein. The reinforcing regions 132 may define the maximum leaflet thickness $T_{max}$ of between about 300-700 microns, while the thinner main portion 134 desirably has a minimum leaflet thickness $T_{min}$ of between about 200-500 microns, and potentially thinner More particularly, for smaller heart valves down to 17 or 19 mm, leaflet tissue having a minimum thickness $T_{min}$ of between 150-250 microns is contemplated, while larger valve such as 26 mm valves may have tissue up to 350 microns. One contemplated embodiment is ultrathin tissue on the order of only 100 microns. The maximum leaflet thickness $T_{max}$ is desirably up to twice the thickness of the thinner portion of the leaflet. In particular example, a smaller valve of 19 mm may have leaflets with $T_{min}$ of between 150-250 microns, while the maximum leaflet thickness $T_{max}$ in the reinforced areas is up to 300-500 microns.

FIGS. 10-12 illustrate alternative thickness profiles in pericardial tissue prosthetic heart valve leaflets from the selective thinning processes described herein. Each of the leaflets is shown in plan view and has an arcuate cusp edge 140, a generally straight free edge 142 opposite the cusp edge, and a pair of oppositely-directed tabs 144 at either end of the free edge. Each of the tabs 144 includes a tapered side 146 which transitions to the free edge 142. A central portion 148 in each of the leaflets forms the fluid occluding surface that oscillates in and out of the flow stream to alternately open and close the valve. This shape is exemplary only, and other leaflet shapes are known. Each of the leaflets shown in FIGS. 10-12 have the same shape, and thus the same element numbers for the shape characteristics will be used.

FIG. 10 illustrates a leaflet 150 having a thickened peripheral edge region 152 in areas where sutures penetrate for attachment to a structural stent (not shown). More particularly, the thickened peripheral edge region 152 extends around the entire cusp edge 140 and up into at least a portion of the tabs 144. As mentioned, these are areas in which sutures are used to attach the leaflet to a supporting stent. The thickness of the peripheral edge region 152 may be up to 700 microns, preferably between 300-700 microns. At the same time, the central portion 148 is formed to have a relatively small thickness, thus facilitating a smaller delivery profile for valves that are compressed. For instance, a uniform thickness of 250 microns for the central portion 148 is believed particularly useful to reduce the crimped profile of collapsible/expandable valves, though uniform thicknesses between 250-500 microns may be suitable.

FIGS. 10A and 10B are sectional views through a radial midline (vertical) of the leaflet of FIG. 10 showing two different thickness profiles. In FIG. 10A, the thicker peripheral edge region 152 transitions to the thinner central portion 148 at a relatively abrupt step 154. In contrast, FIG. 10B illustrates a gradual ramp 156 between the thick edge region 152 and thinner central portion 148. The ramp 156 is shown linear, although other contours such as curved or gradually stepped may be used. It is believed the more gradual ramp 156 provides a more desirable stress distribution and flow over the leaflet. It may be possible to provide gradual transitions by adjusting the laser power application. Another way to accomplish gradual ramps is to use a skiving technology in combination with a forming mold, as described below with reference to FIGS. 14A and 14B.

FIG. 11 is a plan view of a prosthetic heart valve leaflet 158 having a thickened peripheral edge region 152 as seen in FIG. 10, as well as a thickened strip 160 along the free edge 142. Prosthetic heart valves sometimes fail from elongation of the free edge of the leaflet where the leaflets come together, or coapt, which ultimately may cause prolapse of the valve. Providing the thickened strip 160 along the entire free edge 142 reduces the risk of elongation, as the stresses experienced by free edge are proportional to its thickness. FIGS. 11A and 11B again show two different thickness profiles for the leaflets of FIG. 11, wherein the thickened peripheral edge region 152 and thickened strip 160 may transition to the thinner central portion 148 at steps 162 (FIG. 11A) or at gradual ramps 164 (FIG. 11B).

Finally, FIG. 12 illustrates a heart valve leaflet 166 again having the thickened peripheral edge 152 in areas used for attachment to a structural heart valve stent. In addition, the leaflet 166 has a thickened triple point area 168 in middle of the free edge 142 simulating a nodule of Arantius. To clarify, the so-called triple point in a heart valve leaflet is the point where the leaflet comes together (coapts) with the other leaflets in the center of the flow orifice. Because the three leaflets curve into the middle, a gap therebetween at the triple point may be sufficient to cause regurgitation. In native leaflets, the center of the free edge sometimes has a thickened area known as the nodules of Arantius that tends to fill the gap at the triple point. When using uniform thickness pericardial tissue for the leaflets, leakage can only be avoided by having a long coapting surface that requires extra leaflet material. However, that adversely impacts the ability to compress a valve to a low profile, and sometimes results in distortion of the leaflet when it closes which might result in early calcification. By producing a thickened triple point area 168 in each of the leaflets, a nodule of Arantius may be simulated. The exemplary triple point area 168 is shown as a small triangle in the center of the free edge 142, although the shape could be curved such as a semi-circle, or other shapes. Furthermore, the triple point area 168 may be combined with the thickened strip 162 along the free edge 142, such as seen in FIG. 11. Indeed, any of the various thickened regions described herein can be combined with other regions for a desired effect.

FIGS. 12A and 12B show two different thickness profiles for the leaflet 166. FIG. 12A shows abrupt steps between the thinner central portion 148 and both the thickened peripheral edge 152 and the thickened triple point area 168, while FIG. 12B shows gradual transitions at the same locations.

FIG. 13 illustrates an alternative leaflet 170 of the present application that may help reduce sagging in leaflets, which has been found as a cause of failure in some prosthetic heart valves. Resistance to leaflet elongation is directly proportional to leaflet thickness along radial stress lines. Therefore, in addition to a thickened peripheral edge region 152 and a thickened strip 160 along the free edge 142, the leaflet 170 includes a plurality of thickened radial strips 172, 174 extending from approximately the middle of the free edge 142 to the arcuate cusp edge 140. The "radial lines" in this sense are drawn as if the cusp edge 140 was the edge of a circle centered in the middle of the free edge 142, though it should be understood that the cusp edge 140 may not be defined by a single arc, and may not be centered at the free edge 142. Typically, prosthetic the leaflets are symmetric about a radial midline, however, and thus one preferred arrangement includes a thickened radial strip 172 along the midline (vertical), and symmetric thickened radial strips 174 either side of the vertical strip 172. In the illustrated embodiment, there are three strips; a midline strip 172 and two radial strips 174 at approximately 30° angles from the middle strip. It should also be noted that as illustrated, the various thickened strips around the leaflet are of approximately the same width, though such does not have to be the case. For example, the cusp edge strip 160 and radial strips 172, 174 may be substantially thinner than the edge region 152 through which sutures must pass.

As mentioned above, contoured forming molds may be used to create gradual thickness changes in the leaflets described herein. FIGS. 14A and 14B are schematic views of exemplary leaflet skiving processes utilizing such molds. In FIG. 14A, a forming mold 176 includes a leaflet supporting surface having one side 178 lower than another side 180. A milling tool such as a laser 182 passes over an upper surface of a leaflet 184 and can be controlled to remove material to a predetermined reference plane. In this manner, the left edge of the leaflet remains thicker while more material is removed from the right side to result in a thinner leaflet area in that location. In FIG. 14B, a second forming mold 186 includes a leaflet supporting surface having peripheral sides 188 lower than a middle portion 189. Again, when a laser 182 passes over the upper surface of the leaflet 184, and is controlled to remove material down to a reference plane, more material will be removed from the central region of the leaflet. Of course, many different shapes of forming molds are contemplated, those illustrated in FIGS. 14A and 14B being exemplary only.

The resulting uniform membrane is preferably treated to render it generally inert and safe for human implantation. The treatment typically includes immersing the membrane in a chemical solution such as glutaraldehyde for a predefined period of time to rid the tissue of microbial entities, or "bugs." An exemplary quarantine period is about 14 days. Alternatively or in addition, the completed membrane may be treated using capping of calcification nucleation sites and borohydride reduction to mitigate later in vivo calcification.

For instance, one contemplated sequence for conditioning tissue includes first cross-linking the tissue (e.g., bovine pericardium) with a glutaraldehyde-buffered solution. Next, the tissue may be heat treated using a process such as disclosed in U.S. Pat. No. 5,931,969 to Carpentier, issued Aug. 3, 1999, the disclosure of which is expressly incorporated herein by reference. Subsequently, the thickness of the tissue may be reduced using any of the methods disclosed in the present application. Finally, the thinner tissue may be treated with a capping and/or reducing agent to mitigate later in vivo calcification, this may also include treating with a glycerol/ethanol solution. For prosthetic heart valve leaflets, the tissue is then formed into leaflets, attached to a surrounding heart valve support frame or other such components, and sterilized such as with ethylene oxide. After the tissue has been milled, stamped, sliced, laser ablated, drawn down, or extruded to reduce its thickness, calcification nucleation sites (e.g., aldehydes and Schiff bases) may be exposed which creates a propensity for calcification. Treating with a capping agent (e.g., ethanolamine) a reducing agent (e.g., sodium borohydride) and a collagen preserving agent (e.g. glycerol) caps the nucleation sites and preserves the collagen integrity. This allows the tissue to be as durable as it was before it was reduced in thickness. Furthermore, this process will also allow the tissue to be stored in a non-liquid (i.e., glutaraldehyde) environment. In other words, the process is especially suitable for dry storage of the tissue.

As noted above, the membrane may be at least partially cross-linked or "fixed." Cross-linking the collagenous matrix provides stability prior to implantation to retard degeneration. Further, the fixation process generally operates by blocking reactive molecules on the surface of and within the donor tissue, thereby rendering it substantially non-antigenic and suitable for implantation. Fixing bioprosthetic tissue typically involves contacting the tissue with a cross-linking agent, normally a solution. Exemplary fixing solutions for bioprosthetic tissue such as bovine pericardium include glutaraldehyde, formaldehyde, other aldehydes, EDC, polyethylene glycol, etc. Other ways to fix tissue exist, including heating, irradiating, etc. The fixing step can help maintain the pericardium in a particular three-dimensional form if undertaken after the membrane is otherwise prepared.

It should be understood that although cross-linking the tissue results in a somewhat easier to handle workpiece, the thinning may occur prior to cross-linking as well. Likewise, bulk tissue sheet may be thinned first before or after fixing, or leaflets may first be cut from the bulk membrane which are then thinned before or after fixing.

In addition to laser tissue removal described above, various mechanical devices for shearing tissue such as razor or planing devices may be used to remove some of the tissue. For instance, a device having a flat platen over which a planing razor or blade translates may be substituted for the linear laser configuration of FIG. 7. Other physical configurations for creating relative tissue/razor movement are contemplated, such as for instance using a lathe-like razor to smooth the outer surface of the tissue. Each of these devices may be automatically or computer-controlled using an optical surface measuring component to control the depth of cut. Abrasive tissue removal (e.g., sanding or rasping) may also prove suitable, though the grit of the tool should be relatively fine.

An instrument which is a particularly attractive mechanical system for thinning a sheet of pericardial tissue is a dermatome. A dermatome is surgically used to harvest thin slices of skin from a donor area to use for skin grafts, particularly for grade 3 burns or trauma. These devices date from the 1930s and are well known surgical instruments. Dermatomes have been manually, pneumatically or electrically operated. Uniformity of thickness of skin for grafting is not important to the degree needed for a heart valve leaflet.

Figure 15A:
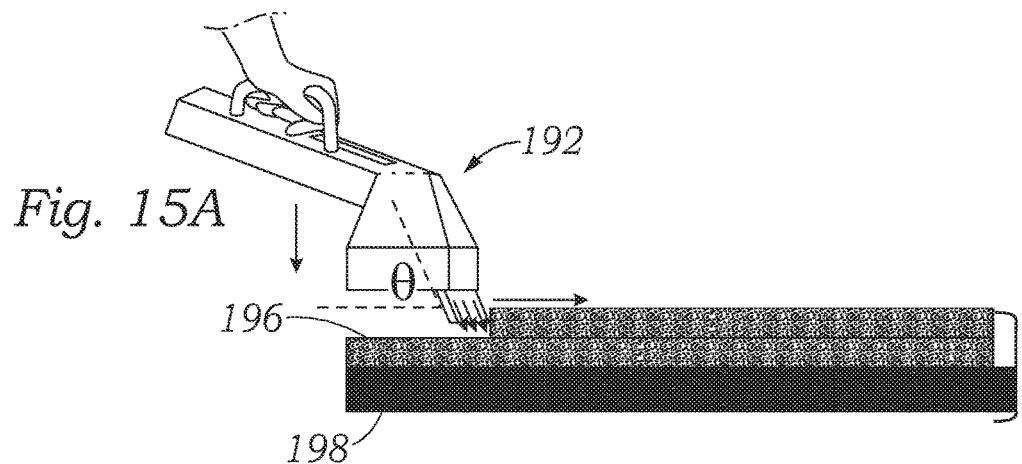
Figure 15B:
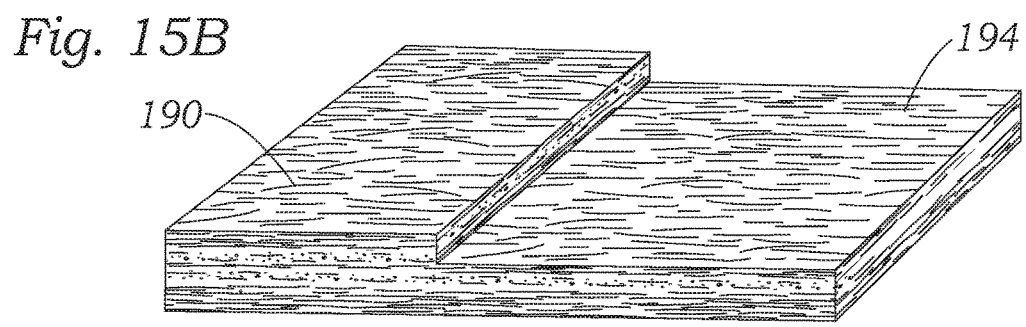
FIG. 15B illustrates the result on a generic section of pericardial tissue.

FIGS. 15A and 15B illustrate a dermatome 192 skiving a rough layer from a generic section of pericardial tissue. Rather than harvesting thin slices of material for use as heart valve leaflets from the membrane, the material 190 removed by the dermatome 192 is discarded in favor of the remaining pericardial membrane 194. To achieve a reliable sheet thickness, spacers 196 are employed upon which the dermatome 192 travels. The surface material 190 shaved from the membrane 194 is the fibrous side of the pericardium. The membrane is placed on a rubber back board 198 and clamped. The back board has a spacer 196 to either side of the membrane to act as rails to support the dermatome 192 as it traverses the membrane 194. The dermatome 192 may also be controlled to limit cutting to a desired pattern so that regions of different heights can be produced. Using a mechanical means to produce a uniform thickness advantageously does not generate heat or chemical effects in the pericardial membrane. It should be understood that as used herein, the term, "dermatome" refers to a dermatome, vibratome, or any other mechanical cutting or abrading device that functions similar to a conventional dermatome for shearing tissue.

To overcome the laser ablated resulting surface reflecting a precut contour in another way, a first compression of the pericardial membrane may be employed. A compression sufficient to flatten surface irregularities and achieve a more uniform thickness may be undertaken before laser ablation. Flattening surface irregularities in this manner helps ensure that the laser ablation step results in a more uniform removal of the surface. Conversely, without compression the laser operation might follow the contour of an irregular surface and remove the same amount of material across its surface, resulting in an irregular end product. One other method to ensure that a regular starting surface is ablated in a manner that results in a smooth surface is to control the laser milling machine using a referencing program that tells the laser to remove material relative to a fixed, uniform surface level, as opposed to following the contours of the surface being milled.

Typical pericardial tissue is in equilibrium at around 78% water; and water can be squeezed from the tissue. Excessive compression to achieve flattening of the fibrous surface and a more uniform thickness can stretch out and break the collagen polymer backbone, eliminating the collagen "crimp" structure and destroying the tissue's intrinsic bioelasticity. Not exceeding the yield point, however, allows the intrinsic bioelasticity to rebound over time. A partial or complete fixing of the pericardial membrane while under elastic compression can retain the advantageous effect of the compression pending laser ablation. Even with reasonably minor compression, some bonds are broken, resulting in some free aldehyde, amine and acid groups. By fixing the pericardial membrane in this gently compressed state, bonds are created to retain this state. Alternatively, the pericardial membrane tends not to fully rebound immediately. Laser ablation immediately following compression can mitigate elastic reexpansion.

Alternatively, a sequence of first conditioning surface irregularities and then compressing the tissue membrane may be employed. For example, larger surface irregularities on the fibrous side of pericardial tissue may be smoothed using a laser, mill, or dermatome, after which the tissue is compressed using various methods as described herein. Preferably, the tissue is compressed while at the same time at least partially fixing the tissue to help prevent spring back. This sequence may yield a more mechanical uniform tissue construct.

As noted above, gentle compression with fixing of the pericardial membrane in the compressed state can smooth the fibrous surface of the pericardium and make the thickness more uniform. This compression and fixing may be employed before or after the thinning of the tissue. After thinning, a stabilization step using capping and borohydride reduction can mitigate later in vivo calcification.

Even greater compression is possible, with or without the ablation or machining process. If laser ablation or a machining process is used, the degree to which the tissue is fixed after compression is somewhat immaterial as a physical trimming rather than further compression is used. If fully fixed at a first, gentle compression, further compression tends to be fully elastic unless the tissue is damaged. A process of partial fixing with gentle compression and then further fixing at greater compression can be used to obtain a thinner final membrane with significant tensile strength.

An initial gentle compression and fixing step is considered above. The process can also proceed without the initial gentle compression, but rather with initially at least partially fixing the tissue. Again, glutaraldehyde or other fixing agent or method may be used. This first fixation sequence stabilizes the biomechanics of the tissue and preserves the natural "crimp" structure of the collagen. Infusion with a second fixing material of sufficient chain length to allow spanning of large inter-fibril domains can then result in a stable membrane. Di- or poly-amine material of substantial chain length may be employed. Other cross-linking materials to span large inter-fibril domains include both linear and branched polyethyleneimine, polyvinyl alcohol and various Jeffamine polymers. Alternatively, the tissue may be oxidized with, for example, sodium chlorite to convert the newly formed aldehydes to carboxylic acids. These may then be coupled with the above amines using EDC chemistry. Compression can occur either at the beginning of the process, of after the infusion with a second fixing material, or both. Laser ablation or machining may be interjected for smoothing or further thinning after either compression step, and/or after the first fixation step. The tissue may be capped and reduced following the first fixation step, or alternatively, the compressed and cross-linked tissue sheet may be stabilized by capping and borohydride reduction after the forming processes. Further treatment can include drying and sterilization. Such processing is described in U.S. Patent Publication No. 2009/0164005, published Jun. 25, 2009 to Dove et al., the disclosure of which is expressly incorporated herein by reference.

Figure 16:
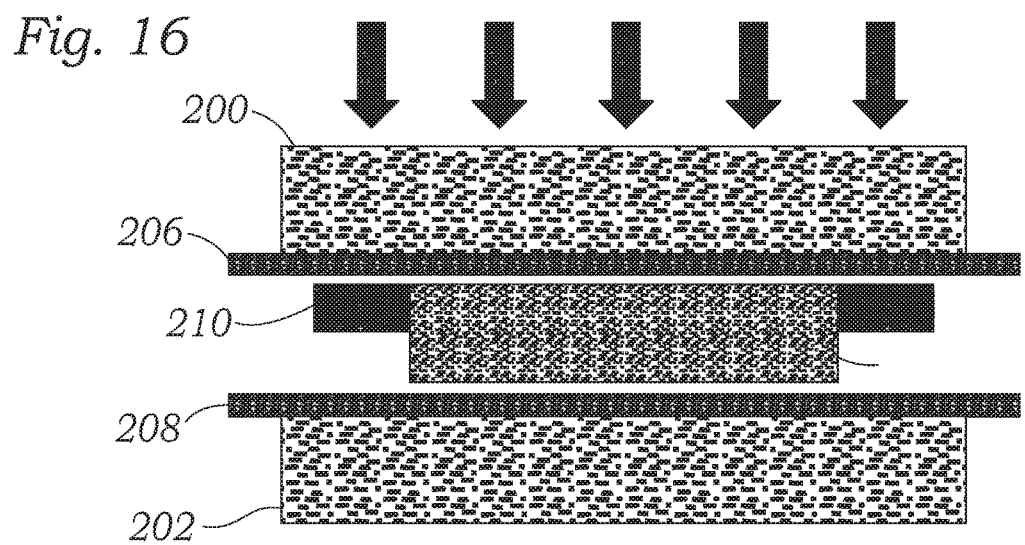
FIG. 16 is a schematic side view of a press with the near spacer removed for clarity.

Apparatus used in any one or all compression steps is illustrated in FIG. 16. Porous ceramic pressure plates 200, 202 are used to provide rigid compression to the tissue 204. Dialysis membranes 206, 208 are interposed between the plates 200, 202 and the tissue 204. The ceramic pressure plates 200, 202 allow free circulation of various chemical treatments into the tissue 204. The disposable dialysis membranes 206, 208 are used to prevent clogging of the ceramic pressure plates 200, 202, preventing the flow of solution during production. Spacers 210 between the ceramic pressure plates 200, 202 to either side of the tissue 204 limits compression.

Another application for the thinning and conditioning processes described herein is in the field of pericardial patches, made from either bovine or equine pericardium. The pericardial patch product may be used as a construction material for tissue repair, such as aortic conduit, pericardium, vessels etc., which is very common in pediatric patients with congenital cardiovascular diseases. One such commercial bovine pericardial patch available from Edwards Lifesciences comes in size of 4×6 inches (10×15 cm), though equine patches can be smaller (3×4 inches). The pericardial patch product is usually treated with a similar process as with heart valve leaflets (may be slightly different for equine patches). One issue is that the pericardial patch may be too thick for some of those applications, so making the patch uniformly thinner would significantly improve its applicability. Also, there is often substantial variability in thickness among the patches and in different locations within any given patch. A desirable uniform thickness for the final product can be ranged from 150 to 500 microns depending on the size of the patch product. The above-described selective thinning may also benefit the patches with one edge or the entire periphery being formed thicker to help retain anchoring sutures.

Thus, improved methods for preparing pericardial material for cardio implantation have been disclosed. While embodiments and applications of this invention have been shown and described, it would be apparent to those skilled in the art that many more modifications are possible without departing from the inventive concepts herein, and it is to be understood that the words which have been used are words of description and not of limitation. Therefore, changes may be made within the appended claims without departing from the true scope of the invention.

What is claimed is:

1. A method for preparing a bioprosthetic tissue comprising:
   treating a bioprosthetic tissue with a first fixative to at least partially fix the tissue;
   treating the bioprosthetic tissue with a collagen preserving agent; and
   reducing a thickness of a pre-determined portion of the bioprosthetic tissue to produce a contoured bioprosthetic tissue having at least two areas of tissue with different thicknesses from one another, wherein the thickness of one of the at least two areas of tissue is up to twice the thickness of another of the at least two areas of tissue.

2. The method of claim 1, wherein the first fixative is an aldehyde.

3. The method of claim 2, wherein the aldehyde is a glutaraldehyde or a formaldehyde.

4. The method of claim 1, wherein the first fixative is a 1-ethyl-3-(3-dimethylaminopropyl)carbodiimide (EDC) or a polyethylene glycol.

5. The method of claim 1, wherein the thickness of the pre-determined portion of the bioprosthetic tissue is in the range of about 150 microns to about 250 microns.

6. The method of claim 1, wherein the thickness of the pre-determined portion of the bioprosthetic tissue is about 100 microns.

7. The method of claim 1, wherein the reducing is performed with a laser.

8. The method of claim 7, wherein the laser is a femtosecond laser.

9. The method of claim 1, wherein the collagen preserving agent comprises glycerol.

10. The method of claim 9, wherein the reducing is performed after treating the bioprosthetic tissue with the collagen preserving agent.

11. The method of claim 1, wherein the reducing is performed by removing material from a fibrous side of the bioprosthetic tissue.

12. The method of claim 11, wherein the removing is performed by ablating the fibrous side of the bioprosthetic tissue with a laser.

13. The method of claim 11, wherein the removing is performed by shearing or milling the fibrous side of the bioprosthetic tissue with a mechanical device.

14. The method of claim 1, wherein the reducing is performed by compressing the bioprosthetic tissue.

15. The method of claim 14, further comprising fixing the bioprosthetic tissue during the compressing using a second fixative.

16. The method of claim 1, further comprising forming heart valve leaflets from the bioprosthetic tissue.

17. The method of claim 16, wherein the forming comprises forming the heart valve leaflets to each have a peripheral edge region, a free edge opposite the peripheral edge region, and a central region surrounded by the peripheral edge region and the free edge.

18. The method of claim 16, further comprising attaching the heart valve leaflets to one or both of a skirt or a stent to form a bioprosthetic heart valve.

19. The method of claim 18, further comprising packaging the heart valve in a non-liquid environment.

20. The method of claim 19, further comprising sterilizing the heart valve following the packaging.

21. A method for preparing a bioprosthetic tissue comprising:
   treating a bioprosthetic tissue with a fixative to at least partially fix the tissue;
   reducing a thickness of a pre-determined portion of the bioprosthetic tissue to produce a contoured bioprosthetic tissue having at least two areas of tissue with different thicknesses from one another, wherein the thickness of one of the at least two areas of tissue is up to twice the thickness of another of the at least two areas of tissue; and
   treating the bioprosthetic tissue with one or both of a capping agent and a reducing agent.

22. The method of claim 21, wherein the bioprosthetic tissue is treated with at least the capping agent and wherein the treating the bioprosthetic tissue with at least the capping agent reduces the propensity of the bioprosthetic tissue to calcify in vivo.

23. The method of claim 22, wherein the treating the bioprosthetic tissue with at least the capping agent caps the calcification nucleation sites associated with the bioprosthetic tissue.

24. The method of claim 23, wherein the capping agent is an ethanolamine.

25. The method of claim 23, further comprising treating the bioprosthetic tissue with a collagen preserving agent before the reducing.

26. The method of claim 21, wherein the bioprosthetic tissue is treated with at least the reducing agent and wherein the treating of the bioprosthetic tissue with at least the reducing agent reduces the propensity of the bioprosthetic tissue to calcify in vivo.

27. The method of claim 26, wherein the reducing agent is a borohydride.

28. The method of claim 21, wherein the bioprosthetic tissue is treated with both the capping agent and the reducing agent.

29. The method of claim 28, further comprising treating the bioprosthetic tissue with a collagen preserving agent before the reducing the thickness of the predetermined portion of the bioprosthetic tissue.

30. The method of claim 29, wherein the bioprosthetic tissue is treated with the capping agent and the reducing agent after the reducing.

31. The method of claim 1, further comprising compressing the bioprosthetic tissue prior to the reducing.

32. The method of claim 31, wherein the compressing is performed during the treating of the bioprosthetic tissue with the first fixative.

33. The method of claim 1, wherein the treating the bioprosthetic tissue with the first fixative is performed prior to the reducing.

34. A method for preparing a bioprosthetic tissue comprising:
   treating a bioprosthetic tissue with a first fixative to at least partially fix the tissue; and
   after the treating, reducing a thickness of a pre-determined portion of the bioprosthetic tissue to produce a contoured bioprosthetic tissue having at least two areas of tissue with different thicknesses from one another.

* * * * *